(12) United States Patent
Henley et al.

(10) Patent No.: US 7,127,285 B2
(45) Date of Patent: Oct. 24, 2006

(54) SYSTEMS AND METHODS FOR ELECTROKINETIC DELIVERY OF A SUBSTANCE

(75) Inventors: Julian L. Henley, New Haven, CT (US); Kuo Wei Chang, Waltham, MA (US); Joseph Potter, Oak Bluffs, MA (US); Dennis I. Goldberg, South Brookline, MA (US); James Derouin, Taunton, MA (US)

(73) Assignee: Transport Pharmaceuticals Inc., West Conshohoken, PA (US)

( * ) Notice: Subject to any disclaimer, the term of this patent is extended or adjusted under 35 U.S.C. 154(b) by 151 days.

(21) Appl. No.: 10/359,559

(22) Filed: Feb. 7, 2003

(65) Prior Publication Data

US 2003/0199808 A1    Oct. 23, 2003

Related U.S. Application Data

(60) Continuation-in-part of application No. 09/523,217, filed on Mar. 10, 2000, now Pat. No. 6,553,253, which is a continuation-in-part of application No. 10/245,337, filed on Sep. 18, 2002, now Pat. No. 6,735,470, which is a continuation-in-part of application No. 10/117,346, filed on Apr. 8, 2002, now Pat. No. 6,792,306, which is a continuation-in-part of application No. 09/584,138, filed on May 31, 2000, now Pat. No. 6,477,410, which is a division of application No. 09/584,138, filed on May 31, 2000, now Pat. No. 6,477,410.

(60) Provisional application No. 60/123,934, filed on Mar. 12, 1999.

(51) Int. Cl.
*A61N 1/30* (2006.01)

(52) U.S. Cl. ............... 604/20; 604/501; 607/148

(58) Field of Classification Search ............... 604/20, 604/21, 501; 607/148, 149, 152, 153
See application file for complete search history.

(56) References Cited

U.S. PATENT DOCUMENTS

| 206,474 A | 7/1878 | Morel |
| 279,524 A | 6/1883 | Beaty ........................ 607/145 |
| 484,522 A | 10/1892 | McBride |

(Continued)

FOREIGN PATENT DOCUMENTS

| AT | OE 0232642 | 3/1964 | ................... 604/20 |

(Continued)

OTHER PUBLICATIONS

"Iontophoretic Treatment of Oral Herpes," Henley et al.; Laryngoscope, vol. 94, No. 1, pp. 118-121, Jan. 1984.

(Continued)

*Primary Examiner*—Henry Bennett
*Assistant Examiner*—Camtu Nguyen
(74) *Attorney, Agent, or Firm*—Nixon & Vanderhye, PC

(57) ABSTRACT

A system for delivering a substance into a body at a treatment site that includes an alternating current source and a plurality of electrodes. Circuitry is connected between the alternating current source and the electrodes for supplying current to the electrodes when the electrodes are in electrical contact with said body so that a uni-directional current flow for delivering the substance into the body is maintained at the treatment site and a bi-directional current flow is maintained throughout the body. At least one of the electrodes is divided into sub-electrodes to, for example, reduce hazards associated with current concentration. These and other systems and methods are adaptable for large treatment areas and/or use a convenient and low-cost arrangement of electronics.

46 Claims, 13 Drawing Sheets

U.S. PATENT DOCUMENTS

| | | | |
|---|---|---|---|
| 600,290 A | 3/1898 | Muir | |
| 1,967,927 A | 7/1934 | Deustch | 604/20 |
| 2,047,308 A | 7/1936 | Chapman | 128/799 |
| 2,123,980 A | 7/1938 | Warwick | |
| 2,126,070 A | 8/1938 | Wappler | |
| 2,834,344 A | 5/1958 | Kanai | |
| 3,019,787 A | 2/1962 | Simmons | |
| 3,048,170 A | 8/1962 | Lemos | |
| 3,107,672 A | 10/1963 | Hofmann | |
| 3,163,166 A | 12/1964 | Brant et al. | |
| 3,298,368 A | 1/1967 | Charos | 128/260 |
| 3,520,297 A | 7/1970 | Bechtold | |
| 3,556,105 A | 1/1971 | Shepard | |
| 3,645,260 A | 2/1972 | Cinotti et al. | |
| 3,716,054 A | 2/1973 | Porter et al. | |
| 3,831,598 A | 8/1974 | Tice | |
| 3,848,600 A | 11/1974 | Patrick, Jr. et al. | 128/783 |
| 4,116,238 A | 9/1978 | Pettijohn | 128/172.1 |
| 4,166,457 A | 9/1979 | Jacobsen et al. | |
| 4,211,222 A | 7/1980 | Tapper | 128/803 |
| 4,292,968 A | 10/1981 | Ellis | 128/207.21 |
| 4,301,794 A | 11/1981 | Tapper | 604/20 |
| 4,325,367 A | 4/1982 | Tapper | |
| 4,383,529 A | 5/1983 | Webster | |
| 4,393,884 A | 7/1983 | Jacobs | 131/273 |
| 4,406,658 A | 9/1983 | Lattin et al. | 604/20 |
| 4,416,274 A | 11/1983 | Jacobsen et al. | 128/803 |
| 4,429,703 A | 2/1984 | Haber | 131/273 |
| 4,474,570 A | 10/1984 | Ariura et al. | 604/20 |
| 4,510,939 A | 4/1985 | Brenman et al. | 128/639 |
| 4,639,244 A | 1/1987 | Rizk et al. | |
| 4,655,229 A | 4/1987 | Sensabaugh, Jr. et al. | 131/273 |
| 4,665,921 A | 5/1987 | Teranishi et al. | |
| 4,689,039 A | 8/1987 | Masaki | |
| 4,702,732 A | 10/1987 | Powers et al. | |
| 4,708,716 A | 11/1987 | Sibalis | 604/20 |
| 4,735,217 A | 4/1988 | Gerth et al. | 131/273 |
| 4,747,819 A | 5/1988 | Phipps et al. | |
| 4,756,318 A | 7/1988 | Clearman et al. | 131/359 |
| 4,763,660 A | 8/1988 | Kroll et al. | 128/798 |
| 4,764,164 A | 8/1988 | Sasaki | 604/20 |
| 4,767,402 A | 8/1988 | Kost et al. | |
| 4,771,796 A | 9/1988 | Myer | 131/273 |
| 4,776,353 A | 10/1988 | Lilja et al. | 131/297 |
| 4,786,278 A | 11/1988 | Masaki | 604/20 |
| 4,787,888 A | 11/1988 | Fox | |
| 4,793,366 A | 12/1988 | Hill | 131/273 |
| 4,800,903 A | 1/1989 | Ray et al. | 131/273 |
| 4,808,152 A | 2/1989 | Sibalis | 604/20 |
| 4,813,437 A | 3/1989 | Ray | 131/273 |
| 4,820,263 A | 4/1989 | Spevak et al. | 604/20 |
| 4,821,740 A | 4/1989 | Tachibana et al. | 604/20 |
| 4,838,273 A | 6/1989 | Cartmell | 600/392 |
| 4,865,582 A | 9/1989 | Sibalis | 604/20 |
| 4,907,606 A | 3/1990 | Lilja et al. | 131/273 |
| 4,913,148 A | 4/1990 | Diethelm | |
| 4,917,119 A | 4/1990 | Potter et al. | 131/273 |
| 4,919,648 A | 4/1990 | Sibalis | 604/20 |
| 4,922,901 A | 5/1990 | Brooks et al. | 128/203.26 |
| 4,931,046 A | 6/1990 | Newman | 604/20 |
| 4,942,883 A | 7/1990 | Newman | 604/20 |
| 4,950,229 A | 8/1990 | Sage, Jr. | 604/20 |
| 4,953,565 A | 9/1990 | Tachibana et al. | 604/20 |
| 4,957,480 A | 9/1990 | Morenings | |
| 4,979,938 A | 12/1990 | Stephen et al. | |
| 4,997,418 A | 3/1991 | DeMartini | |
| 5,002,527 A | 3/1991 | Reller et al. | |
| 5,006,108 A | 4/1991 | LaPrade | 604/20 |
| 5,019,034 A | 5/1991 | Weaver et al. | 604/20 |
| 5,037,381 A | 8/1991 | Bock et al. | |
| 5,042,975 A | 8/1991 | Chien et al. | |
| 5,047,007 A | 9/1991 | McNichols et al. | 604/20 |
| 5,060,671 A | 10/1991 | Counts et al. | 131/329 |
| 5,090,402 A | 2/1992 | Bazin et al. | |
| 5,115,805 A | 5/1992 | Bommannan et al. | |
| 5,133,352 A | 7/1992 | Lathrop et al. | |
| 5,135,478 A | 8/1992 | Sibalis | |
| 5,135,479 A | 8/1992 | Sibalis et al. | 604/20 |
| 5,147,291 A | 9/1992 | Cukier | 604/22 |
| 5,160,316 A | 11/1992 | Henley | 604/20 |
| 5,162,042 A | 11/1992 | Gyory et al. | |
| 5,167,242 A | 12/1992 | Turner et al. | 131/273 |
| 5,169,384 A | 12/1992 | Bosniak et al. | |
| 5,171,215 A | 12/1992 | Flanagan | 604/20 |
| 5,203,768 A | 4/1993 | Haak et al. | |
| 5,250,022 A | 10/1993 | Chien et al. | |
| 5,254,081 A | 10/1993 | Maurer et al. | 604/20 |
| 5,279,543 A | 1/1994 | Glikfeld et al. | |
| 5,284,471 A | 2/1994 | Sage, Jr. | |
| 5,298,017 A | 3/1994 | Theeuwes et al. | |
| 5,310,404 A | 5/1994 | Gyory et al. | |
| 5,312,326 A | 5/1994 | Myers et al. | |
| 5,314,502 A | 5/1994 | McNichols et al. | |
| 5,331,979 A | 7/1994 | Henley | |
| 5,354,321 A | 10/1994 | Berger | |
| 5,360,440 A | 11/1994 | Andersen | |
| 5,362,307 A | 11/1994 | Guy et al. | |
| 5,362,308 A | 11/1994 | Chien et al. | |
| 5,374,241 A | 12/1994 | Lloyd et al. | |
| 5,374,242 A | 12/1994 | Haak et al. | |
| 5,376,107 A | 12/1994 | Inagi et al. | |
| 5,391,195 A | 2/1995 | Van Groningen | |
| 5,395,310 A | 3/1995 | Untereker et al. | |
| 5,413,590 A | 5/1995 | Williamson | |
| 5,415,629 A | 5/1995 | Henley | |
| 5,421,816 A | 6/1995 | Lipkovker | |
| 5,441,936 A | 8/1995 | Houghten et al. | |
| 5,443,441 A | 8/1995 | De Claviere | |
| 5,458,569 A | 10/1995 | Kirk, III et al. | 604/20 |
| 5,464,387 A | 11/1995 | Haak et al. | |
| 5,466,217 A | 11/1995 | Myers et al. | |
| 5,470,349 A | 11/1995 | Kleditsch et al. | |
| 5,494,679 A | 2/1996 | Sage, Jr. et al. | |
| 5,501,705 A | 3/1996 | Fakhri | |
| 5,514,167 A | 5/1996 | Smith et al. | |
| 5,538,503 A | 7/1996 | Henley | |
| 5,540,669 A | 7/1996 | Sage, Jr. et al. | 604/20 |
| 5,551,953 A | 9/1996 | Lattin et al. | |
| 5,558,632 A | 9/1996 | Lloyd et al. | |
| 5,562,607 A | 10/1996 | Gyory | |
| 5,589,563 A | 12/1996 | Ward et al. | |
| 5,603,693 A | 2/1997 | Frenkel et al. | |
| 5,607,461 A | 3/1997 | Lathrop | |
| 5,607,691 A | 3/1997 | Hale et al. | |
| 5,618,275 A | 4/1997 | Bock | |
| 5,658,247 A | 8/1997 | Henley | |
| 5,667,487 A | 9/1997 | Henley | |
| 5,668,170 A | 9/1997 | Gyory | |
| 5,676,648 A | 10/1997 | Henley | |
| 5,678,273 A | 10/1997 | Porcelli | |
| 5,688,233 A | 11/1997 | Hofmann et al. | |
| 5,697,896 A | 12/1997 | McNichols et al. | |
| 5,700,457 A | 12/1997 | Dixon | |
| 5,711,761 A | 1/1998 | Untereker et al. | |
| 5,713,846 A | 2/1998 | Bernhard et al. | |
| 5,722,397 A | 3/1998 | Eppstein | |
| 5,725,817 A | 3/1998 | Milder | |
| 5,733,255 A | 3/1998 | Dinh et al. | |
| 5,755,750 A | 5/1998 | Petruska et al. | |
| 5,788,666 A | 8/1998 | Atanasoska | |
| 5,794,774 A | 8/1998 | Porcelli | |
| 5,795,321 A | 8/1998 | McArthur et al. | |
| 5,797,867 A | 8/1998 | Guerrera et al. | |
| 5,830,175 A | 11/1998 | Flower | |

| | | |
|---|---|---|
| 5,840,057 A | 11/1998 | Aloisi |
| 5,846,217 A | 12/1998 | Beck et al. |
| 5,865,786 A | 2/1999 | Sibalis et al. .................. 604/20 |
| 5,879,323 A | 3/1999 | Henley |
| 5,882,676 A | 3/1999 | Lee et al. |
| 5,899,875 A | 5/1999 | Millot |
| 5,899,876 A | 5/1999 | Flower ......................... 604/20 |
| 5,908,401 A | 6/1999 | Henley ......................... 604/20 |
| 5,911,319 A | 6/1999 | Porcelli et al. |
| 5,919,155 A | 7/1999 | Lattin et al. .................. 604/20 |
| 5,931,859 A | 8/1999 | Burke |
| 5,935,598 A | 8/1999 | Sage et al. |
| 5,954,684 A | 9/1999 | Flower et al. ................ 604/20 |
| 5,961,482 A | 10/1999 | Chien et al. |
| 5,961,483 A | 10/1999 | Sage et al. |
| 5,968,005 A | 10/1999 | Tu |
| 5,968,006 A | 10/1999 | Hofmann |
| 5,983,130 A | 11/1999 | Phipps et al. |
| 6,004,309 A | 12/1999 | Phipps |
| 6,004,547 A | 12/1999 | Rowe et al. |
| 6,006,130 A | 12/1999 | Higo et al. |
| 6,018,679 A | 1/2000 | Dinh et al. |
| 6,023,639 A | 2/2000 | Hakky et al. |
| 6,032,073 A | 2/2000 | Effenhauser |
| RE36,626 E | 3/2000 | Henley |
| 6,038,485 A | 3/2000 | Axelgaard |
| 6,041,252 A | 3/2000 | Walker et al. |
| 6,041,253 A | 3/2000 | Kost et al. |
| 6,048,545 A | 4/2000 | Keller et al. |
| 6,057,374 A | 5/2000 | Huntington et al. |
| 6,101,411 A | 8/2000 | Newsome |
| 6,148,231 A | 11/2000 | Henley ......................... 604/20 |
| 6,148,232 A | 11/2000 | Avrahami ..................... 604/20 |
| 6,167,302 A | 12/2000 | Millot |
| 6,267,736 B1 | 7/2001 | McCambridge et al. |
| 6,385,487 B1 | 5/2002 | Henley ......................... 604/20 |
| RE37,796 E | 7/2002 | Henley ......................... 604/20 |
| 6,477,410 B1 | 11/2002 | Henley et al. |
| RE38,000 E | 2/2003 | Henley |
| 6,553,253 B1 | 4/2003 | Chang .......................... 604/20 |
| RE38,341 E | 12/2003 | Henley |
| 6,735,470 B1 | 5/2004 | Henley et al. ................ 604/20 |
| 6,792,306 B1 | 9/2004 | Henley et al. |
| 6,895,271 B1 | 5/2005 | Henley |
| 2004/0039328 A1 | 2/2004 | Henley |
| 2004/0111051 A1 | 6/2004 | Henley et al. |
| 2004/0176737 A1 | 9/2004 | Henley et al. |
| 2005/0182351 A1 | 8/2005 | Henley et al. |

FOREIGN PATENT DOCUMENTS

| | | | |
|---|---|---|---|
| EP | 0230749 | 8/1987 | .................. 604/20 |
| EP | 0309093 A1 | 3/1989 | .................. 604/20 |
| EP | 617979 A1 | 10/1994 | |
| FR | 1445703 | 6/1966 | .................. 604/20 |
| FR | 2 513 129 | 3/1983 | |
| GB | 0299553 | 11/1928 | .................. 604/20 |
| GB | 1 485 170 | 9/1977 | |
| JP | 3-170172 | 7/1991 | |
| SU | 654254 | 3/1979 | |
| SU | 931191 | 5/1982 | |
| SU | 1003853 | 3/1983 | |
| WO | 07269 | 12/1986 | .................. 604/20 |
| WO | WO 90/06153 | 6/1990 | |
| WO | 08571 | 8/1990 | .................. 604/20 |
| WO | 03790 | 3/1993 | .................. 604/20 |

OTHER PUBLICATIONS

"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp. 105-109 (1979).

"Iontophoresis of Vidarabine Monophosphate for Herpes Orolabialis," Gangarosa et al.; The Journal of Infectious Diseases, vol. 154, No. 6, pp. 930-934, Dec. 1986.

"The Natural History of Recurrent Herpes Simplex Labialis," Spruance et al.; The New England Journal of Medicine, vol. 297, No. 2, pp. 69-75, Jul. 14, 1977.

"Infection with Herpes-Simplex Viruses 1 and 2," Nahmias et al.; The New England Journal of Medicine, pp. 667-674, Sep. 27, 1973.

"Anesthesia of the Human Tympanic Membrane by Iontophoresis of a Local Anesthetic," Comeau et al.; The Laryngoscope, 88:1978, pp. 277-285.

"Iontophoretic Application of Drugs," Waud, J. Appl. Physiol. 23(1), 1967, pp. 128-130.

"Antibiotic Iontophoresis in the Treatment of Ear Chondritis," LaForest et al., Physical Therapy, vol. 58, No. 1, Jan. 1978, pp. 32-34.

"The Quantity and Distribution of Radiolabeled Dexamethasone Delivered to Tissue by Iontophoresis," Glass et al.; International Journal of Dermatology, vol. 19, Nov. 1980, pp. 519-525.

"Iontophoretic Application of Antiviral Chemotherapeutic Agents," Hill et al., Annals New York Academy of Sciences, pp. 604-612.

"Ocular Iontophoresis," Hill et al. Paper, Louisiana State University Medical Center, School of Medicine, New Orleans, Louisiana, pp. 331-354.

"Iontophoretic Application of Adenine Arabinoside Monophosphate to Herpes Simplex Virus Type 1-Infected Hairless Mouse Skin," Park et al.; Antimicrobial Agents and Chemotherapy, vol. 14, No. 4, Oct. 1978, pp. 605-608.

"Iontophoresis: Applications in Transdermal Medication Delivery," Costello et al.; Physical Therapy, vol. 75, No. 6, pp. 104/554-113/563, Jun. 1995.

Physical Enhancement of Dermatologic Drug Delivery: Iontophoresis and Phonophoresis, Kassan et al., Journal of the American Academy of Dermatology, Apr. 1996, pp. 657-666.

"Iontophoresis and Herpes Labialis," Boxhall et al.; The Medical Journal of Australia, May 26, 1984, pp. 686-687.

"Iontophoresis: A Method of Antibiotic Administration in the Burn Patient," Rapperport et al., Plastic and Reconstructive Surgery, 1965, vol. 36, No. 5, pp. 547-552.

"Iontophoresis for Enhancing Penetration of Dermatologic and Antiviral Drugs," Gangarosa et al., Journal of Dermatology, vol. 22, No. 11, pp. 865-875, Nov. 1995.

"Iontophoretic Treatment of Herpetic Whitlow," Gangarosa et al., Arch. Phys. Med. Rehabil., vol. 70, pp. 336-340Apr. 1989.

"Iontophoretic Application of Antiviral Drugs," Gangarosa et al., Proceedings of an International Symposium held in Tokushima City, Japan, pp. 201-204, Jul. 27-30, 1981.

"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, pp. 1014, Dec. 1979.

"Effect of Iontophoretic and Topical Application of Antiviral Agents in Treatment of Experimental HSV-1 Keratitis in Rabbits," Kwon et al., Investigative Ophthalmology & Visual Science, vol. 18, No. 9, pp. 984-988, Sep. 1979.

"Acyclovir and Vidarabine Monophosphate: Comparison of Iontophoretic and Intravenous Administration for the Treatment of HSV-1 Stromal Keratitis," Hill et al., The American Journal of Medicine, Acyclovir Symposium, pp. 300-304.

"Thymine Arabinoside (Ara-T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17-20, 1984.

"Iontophoresis Enhances the Transport of Acyclovir Through Nude Mouse Skin by Electrorepulsion and Electroosmosis," Volpato et al., Pharmaceutical Research, vol. 12, No. 11, pp. 1623-1627, 1995.

"Early Application of Topical 15% Idoxuridine n Dimethyl Sulfoxide Shortens the Course of Herpes Simplex Labialis: A Multicenter Placebo-Controlled Trial," Spruance et al., The Journal of Infectious Diseases, 1990; vol. 161; pp. 191-197.

"Iontophoresis for Surface Local Anesthesia," Gangarosa, JADA, vol. 88, pp. 125-128, Jan. 1974.

"Conductivity of Drugs Used for Iontophoresis," Gangarosa et al., Journal of Pharmaceutical Sciences, vol. 67, No. 10, pp. 1439-1443, Oct. 1978.

"A Pilot Study of Iontophoretic Cisplatin Chemotherapy of Basal and Squamous Cell Carcinomas of the Skin," Chang et al., Arch. Dermatol., vol. 129, pp. 425-427, Apr. 1993.

"How Modern Iontophoresis Can Improve Your Practice," Gangarosa et al., (Quintessence International) Oral Surgery, No. 10, Report 2135, Oct. 1982, pp. 1027-1038.

"Postherpetic Neuralgia," Baron et al., Brain (1993), 116, pp. 1477-1496.

"Iontophoretic Assistance of 5-Iodo-2'-Deoxyuridine Penetration into Neonatal Mouse Skin and Effects of DNA Synthesis," Gangarosa et al., Society for Experimental Biology and Medicine, pp. 439-443, 1977.

"Electrophoretic Evaluation of the Mobility of Drugs Suitable for Iontophoresis," Kamath et al., Meth. Find. Exp. Clin. Pharmacol., 1995, 17(4): pp. 227-232.

"Transdermal Drug Delivery by Passive Diffusion and Iontophoresis: A Review," Singh et al., Medicinal Research Reviews, vol. 13, No. 5, 1993, pp. 569-621.

"Iontophoresis: Electrorepulsion and Electroosmosis," Guy et al., Journal of Controlled Release 64 (2000) 129-132.

"Treatment of Common Cutaneous Herpes Simplex Virus Infections," Emmert, American Family Physician, vol. 61, No. 6, Mar. 15, 2000, pp. 1697-1704.

"Gelatin-stabilised Microemulsion-Based Oranogels: Rheology and Application in Iontophoretic Transdermal Drug Delivery," Kantaria et al., Journal of Controlled Release 60 (1999) 355-365.

"Electrorepulsion Versus Electroosmosis: Effect of pH on the Iontophoretic Flux of 5-Fluorouracil," Merino et al., Pharmaceutical Research, vol. 16, No. 6 (1999).

"Azelaic Acid: Potential as a General Antitumoural Agent," Breathnach, Medical Hypotheses (1999) 52(3) 221-226.

"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301-306.

"Efficacy and Safety of Azelaic Acid and Glycolic Acid Combination Therapy Compared with Tretinoin Therapy for Acne," Spellman et al., Clinical Therapeutics, vol. 20, No. 4, 1998, pp. 711-721.

"Passive Versus Electrotransport-Facilitated Transdermal Absorption of Ketorolac," Park et al., Clinical Pharmacology & Therapeutics, vol. 63, No. 3, pp. 303-315.

"Soriudine Versus Acyclovir for Treatment of Dermatomal Herpes Zoster in Human Immunodeficiency Virus-Infected Patients: Results from a Randomized, Controlled Clinical Trial," Gnann et al., Antimicrobial Agents and Chemotherapy, vol. 42, No. 5, May 1998, pp. 1139-1145.

"Azelaic Acid 20% Cream (AZELEX®) and the Medical Management of Acne Vulgaris," Gibson, Dermatology Nursing, vol. 9, No. 5, pp. 339-344.

"Sorivudine: A Promising Drug for the Treatment of Varicella-Zoster Virus Infection," Whitley, Neurology 1995; 45 (Supp. 8), pp. S73-S75.

"Antiherpesviral and Anticellular Effects of 1-β-D-Arabinofuranosyl-E-5-(2-Halogenovinyl) Uracils," Machida et al., Antimicrobial Agents and Chemotherapy, Jul. 1981, pp. 47-52.

"Herpes Simplex," American Academy of Dermatology, 1987, Revised 1991, 1993.

"'Common Cold' Virus is Near," Haney, The Associated Press, Jan. 15, 2000.

"New Medicines Move to Eradicate Acne," Hemphill, The New York Times, Feb . 29, 2000.

"Warts," American Academy of Dermatology, American Academy of Dermatology, 1997, Revised 1991, 1993.

"Psoriasis," American Academy of Dermatology, 1994.

"Eczema/Atopic Dermatitis," American Academy of Dermatology, 1987, Revised 1991, 1993, 1995.

"Skin Cancer: An Undeclared Epidemic," American Academy of Dermatology, 1988, Revised 1989, 1993, 1994.

"Electrophoretically Controlled Dermal or Transdermal Application Systems with Electronic Indicators," Gröning, International Journal of Pharmacuetics, 36 (1987), pp. 37-48.

Source Risk-Current Limits

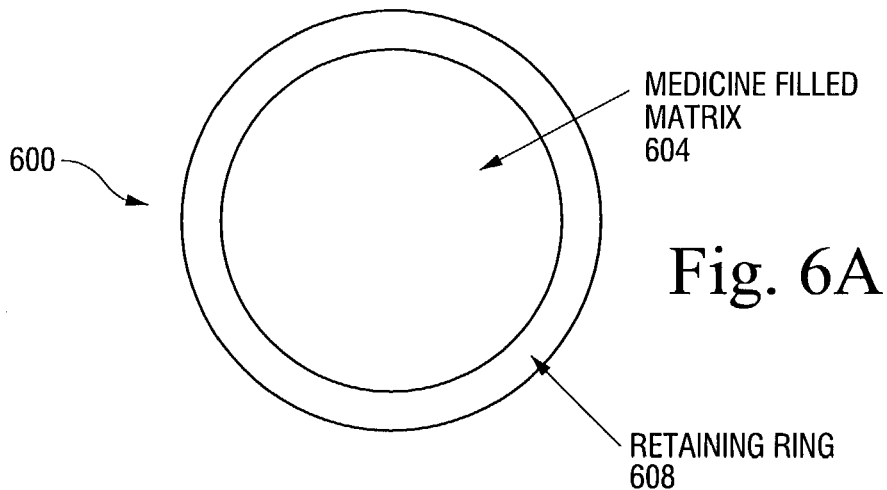
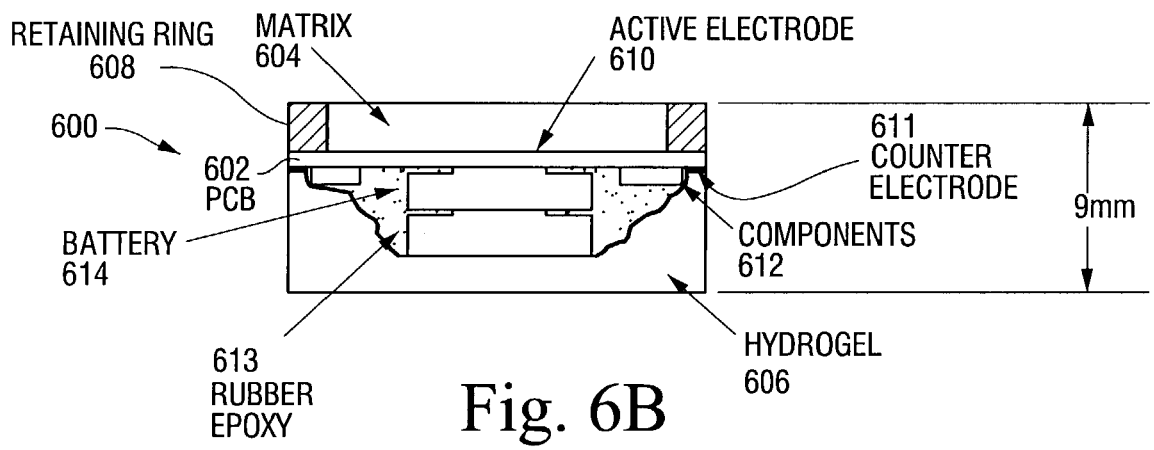
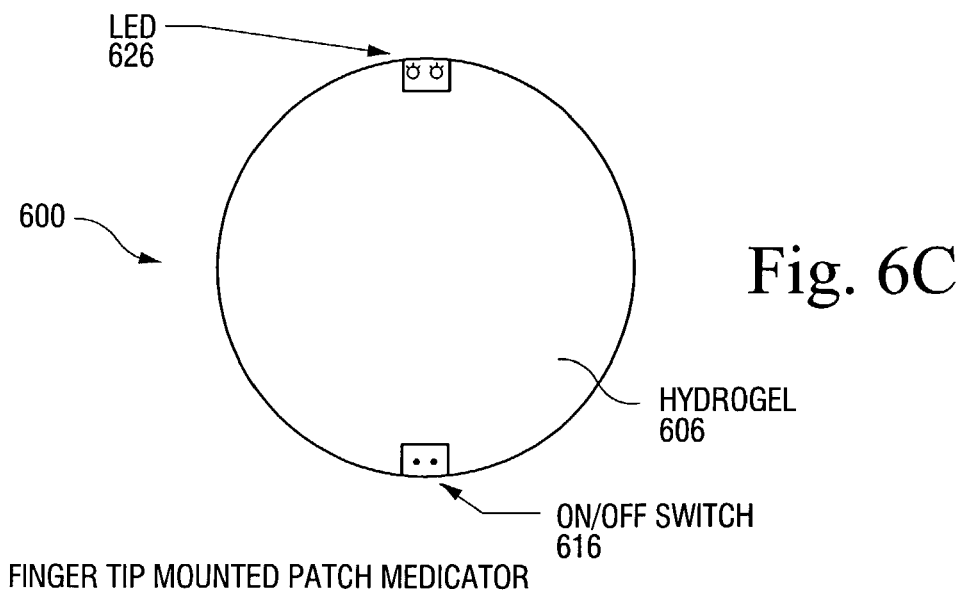
FINGER TIP MOUNTED PATCH MEDICATOR

Fig. 8A
DEVICE STATE

| User Action | Device State | Example Required Condition(s) | Device Response | LED Status | Comments |
|---|---|---|---|---|---|
| Activate Device | ACTIVATE | Jumper shorted, on-switch activated, etc. | Circuit Energized Initialize Processor | None | |
| None Required | SUPRESSED | Circuit Energized | Momentary Flash LED Red/Green | Flash Red/Green | Lasts a few milliseconds |
| None Required | POST(diagnostic) | Circuit Energized | Initiate POST diagnostic test(s) | Flashing green | ~5 sec |
| None Required | READY | Successful POST | Check TREATMENT Counter – if = 6 then goto ERROR<br>Initiate READY Timer – goto OFF if >5min<br>Monitor for treatment current (I > 50uA) | Flashing Green | Do not allow more than 6 treatments<br>If device activated but user fails to apply to face within 5 min – device goes to OFF |
| Holds Device steadily on face | RAMP-UP | 0< Current <368 | Increment TREATMENT Counter (write to NOVRAM)<br>When current reaches 368uA go to TREATMENT<br>If current doesn't reach 368μamps after 5 mins, go to OFF | Flashing Green | |
| Holds Device steadily on face | TREATMENT | 368<= Current <=432 | Start TREATMENT Timer<br>Monitor for interrupts, faults, low battery | Steady Green | |
| User re-positions device for comfort | TRANSIENT | Current<368 for 0 to 2 sec | No interrupt triggered. TREATMENT Timer is paused for time that treatment current was < 368. | Flashing Green | Pausing TREATMENT Timer ensures that fidgety user (several interruptions <2 sec) still gets 10 min dose |
| User removes device from face and/or deactivates device. | INTERRUPTION | Current<368 for >2 sec | Set current to 0<br>Discharge treatment electrode<br>Increment INTERRUPT Counter – if >1goto T-FAULT<br>Start INTERRUPT Timer – if >=30 sec goto T-FAULT<br>Go to RAMP-UP | Flashing Green | |
| None Required | T-FAULT | Interrupt Timer >=30 sec or Interrupt Counter >1 | Set current to 0<br>1 minute wait<br>Goto LOCKOUT | Flashing Red | Treatment Fault |

Fig. 8B

| User Action | Device State | Example Required Condition(s) | Device Response | LED Status | Comments |
|---|---|---|---|---|---|
| None Required | ERROR | Unsuccessful POST<br>Watchdog failure<br>Low Battery voltage<br>Current > 432 µamps | 1 minute wait<br>Goto OFF | Flashing Red | |
| User properly completes 10 min treatment | DONE | Treatment Timer = 10 min | 1 minute wait<br>Go to LOCKOUT | Steady Amber | |
| None Required | LOCKOUT | T-FAULT<br>DONE | Start LOCKOUT Timer – if >24 hr goto OFF | Periodic Flash Red | Processor powered, ignores all other activity – only way to interrupt is to remove battery. Flash Rate is approx. once every 30 sec |
| None Required | OFF | READY Timer > 5 min<br>Or<br>LOCKOUT Timer >24hr<br>Or<br>Current failed to reach 368 µamps<br>Or<br>Initial Battery Install | Wait for Activation | None | Processor not powered |

FINGER TIP MOUNTED PATCH MEDICATOR

SYSTEMS AND METHODS FOR ELECTROKINETIC DELIVERY OF A SUBSTANCE

CROSS-REFERENCES TO RELATED APPLICATIONS

This application is a continuation-in-part of application Ser. No. 09/523,217, filed Mar. 10, 2000 now U.S. Pat 6,553,253, which claims priority from U.S. Application No. 60/123,934, filed Mar. 12, 1999; of application Ser. No. 10/245,337, filed Sep. 18, 2002, which is a divisional of application Ser. No. 09/584,138, filed May 31, 2000, now U.S. Pat. No. 6,477,410; and of application Ser. No. 10/117, 346, filed Apr. 8, 2002 which is a continuation-in-part of application Ser. No. 09/584,138, filed May 31, 2000, now U.S. Pat. No. 6,477,410.

The contents of each of these applications are incorporated herein in their entirety.

BACKGROUND OF THE INVENTION

The present invention generally relates to the electrokinetic delivery of a substance (for example, a medicament) into a treatment site, e.g., tissue and, more particularly, to systems and methods for such delivery that satisfy certain risk criteria for current leakage of medical equipment that maintains direct electrical contact with human skin, that are adaptable for large treatment areas and/or that use a convenient and low-cost arrangement of electronics. The majority of applications using the present invention are for applying medicaments to treatment sites and therefore the term medicament is sometimes used in lieu of the term substance in this description. However, the use of the term "medicament" in a particular instance is not intended to exclude the possibility of using other, non-medicament substances.

One type of electrokinetic delivery mechanism is iontophoresis. Iontophoresis is the transfer of ionic agents into tissue by means of electricity. The active component of the medicament, either directly ionizable or attached to a carrier ion and either positively or negatively charged, is driven into the tissue by a properly biased electrode through barriers to treatment sites such as animal (including human) skin, cell and mucosal membranes and other barrier surfaces. Iontophoresis has been used to deliver, among other things, morphine HCL for postoperative pain relief, topical anesthetics (such as lidocaine) for transdermal anesthetization, anti-viral agents for herpes infection, and anti-fungal medicines for onychomycosis, for example, nail bed (finger and toe) fungal infections or athlete's foot. The use of iontophoretic transdermal or transmucocutaneous delivery techniques obviates the need for hypodermic injection for many medicaments, thereby eliminating the concomitant problems of trauma, pain and risk of infection to the patient. Such delivery techniques may also be utilized for controlled or localized treatment especially when a substantial systemic involvement of the medicament is unwanted or harmful.

Regardless of the charge of the medicament to be administered, conventional iontophoretic delivery devices typically employ two electrodes (an anode and a cathode). In conjunction with the patient's skin or mucosa, the first (applicator or treatment) electrode is positioned at a treatment site on the skin or mucosa, and the second (counter) electrode is affixed to a second site on the skin or mucosa. These electrodes form a current path that enhances the rate of penetration of the medicament into the treatment site adjacent to the applicator electrode. A conventional iontophoretic delivery system 100 is shown in FIG. 1. System 100 includes a treatment electrode (anode) 102 and a counter electrode (cathode) 104 connected to a DC power supply 106. Electrodes 102 and 104 are in electrical contact with the skin or mucosa via conductive layers 110 and 112, respectively. Such layers may be part of a single medicament-carrying substrate. The medicament-carrying substrate is generally disposable and non-reusable and may be releasably adherable to the patient's treatment site and/or to electrodes 102 and 104 or merely interposed in between treatment site and electrodes. Conductive layers 110 and 112 are shown in FIG. 1 as comprising a medicine-soaked sponge (e.g., a morphine HCL-soaked sponge) and a saline-soaked sponge, respectively. In use, iontophoretic device 100 is turned on (e.g., by a switch, not shown) and a current flows from treatment electrode 102, through conductive layer 110 and skin plus underlying tissue 108, to counter electrode 104, thereby driving medicament through the treatment site into the skin and underlying tissue.

Although use of alternating current has been reported (see, e.g., U.S. Pat. No. 5,224,927 to Tapper, Jul. 6, 1993), direct current is generally preferred in iontophoresis. As set forth in the '927 patent, at AC frequencies higher than approximately 10 Hz, no substantial effective drug delivery takes place. Medicament and other ions merely move to and fro, lacking any net unidirectional movement. For DC iontophoresis, the amount of current used varies from 0.2 to 1 milliampere, which exceeds the risk-current limit of 10 microamperes established for current leakage of medical equipment that maintains direct electrical contact with the patient. There exists, therefore, a potential hazard associated with ventricular fibrillation and cardiac arrest if the current generated during iontophoresis accidentally passes through the patient's heart. In iontophoresis, the rate of drug delivery increases with current. For this reason, higher current is, in principle, always favored because treatment time is proportionally reduced. However, for current exceeding 0.5 to 1 milliampere, the patient may feel an uncomfortable burning sensation. Even at the 0.5 to 1 milliampere range, when the treatment area is relatively small, the resulting high current density can possibly cause pain and burning and destruction of the skin tissue.

In any case, to remain effective, existing iontophoresis devices may use treatment currents exceeding the established risk-current limit for equipment leakage. In order to reduce the ventricular fibrillation risk, some devices limit the separation distance between the treatment and the counter electrode so that the heart is not directly in the current path and is therefore less likely to be included within the fringe electric fields created by the electrodes. However, because electric current always flows through a path of least resistance, i.e., a path of shorter distance along the skin, the electrode separation distance needs to be large enough so that current is not short-circuited or concentrated between proximal edges of the electrodes (i.e., between edges 120 and 130 in FIG. 1), so that the current distribution under the treatment electrode is relatively uniform for effective drug delivery, and so that there are no hot-spots or areas of high current density to cause discomfort and pain. Some iontophoretic devices use a large separation distance to obtain a more uniform current distribution by placing the counter electrode in a less accessible and awkward location such as the back or the rear shoulder of the patient.

An effective method for self-administration of a medicament into an individual's skin is disclosed in U.S. Pat. No. 5,676,648 and uses a small cylindrical probe in which the treatment applicator electrode is located at the distal end of a counter electrode consisting of a circumferential tactile metal band which provides electrical connection to the individual's finger and hand. The individual's body completes a long electrical circuit path (through the arm and torso), and thus a uniform current distribution and effective medicament delivery is assured.

BRIEF SUMMARY OF THE INVENTION

In accordance with one aspect of the present invention, a system and method for delivering a substance into a body at a treatment site use an alternating current source and a plurality of electrodes. Circuitry is connected between the alternating current source and the electrodes for supplying current to the electrodes when the electrodes are in electrical contact with said body so that a uni-directional current flow for delivering the substance into the body is maintained at the treatment site and a bi-directional current flow is maintained throughout the body. At least one of the electrodes is divided into sub-electrodes to, for example, reduce hazards associated with current concentration.

In accordance with another aspect of the present invention, a system and method for delivering a substance into a user's body at a treatment site use a printed circuit board on which is provided processing circuitry, a counter electrode and a treatment (active or applicator) electrode. The treatment electrode and counter electrode are formed on opposite sides of the printed circuit board. A substance is in contact with the treatment electrode, which is adapted for electrical contact with the user's body at the treatment site. A conductive gel may be in contact with the counter electrode and adapted for electrical contact with a user's body part such as a finger.

The accompanying drawings, which are incorporated in and constitute a part of the specification, illustrate various embodiments of the present invention and, together with the general description given above and the detailed description provided below, serve to explain the principles of the invention.

BRIEF DESCRIPTION OF THE DRAWINGS

FIGS. 6A–6C are top plan, cross-sectional, and bottom plan views of a patch medicator.

FIGS. 8A and 8B illustrate an example system state table showing device states and the conditions and responses that occur in each.

DETAILED DESCRIPTION

Figure 1:
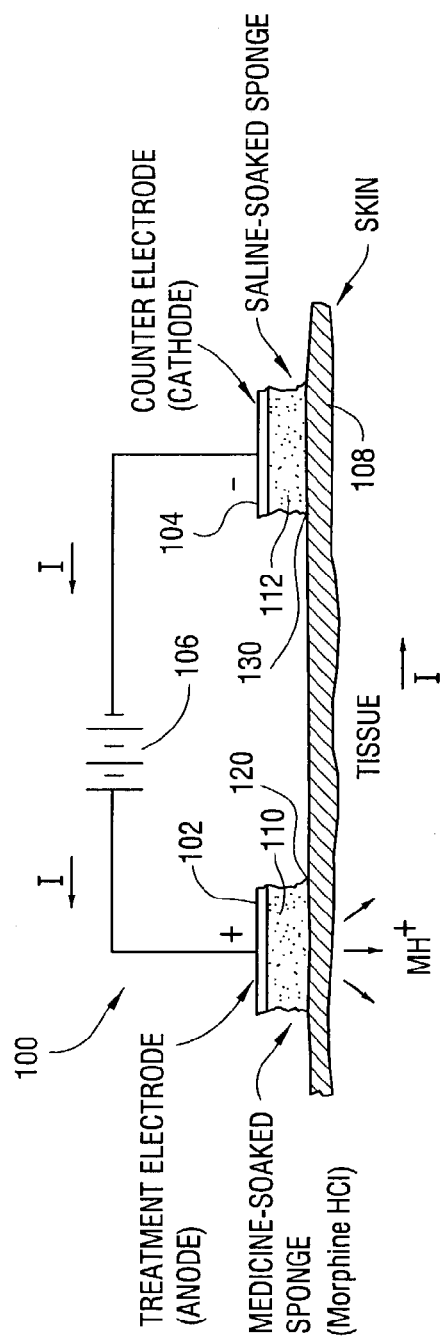
FIG. 1 shows a conventional iontophoretic delivery system 100.

The present invention is described in the context of exemplary embodiments. However, the scope of the invention is not limited to the particular examples and embodiments described in this specification. Rather the specification merely reflects certain embodiments and serves to illustrate the principles and characteristics of the present invention. Those skilled in the art will recognize that various modifications and refinements may be made without departing from the spirit and scope of the invention.

The systems and methods described herein are usable to deliver a substance to a treatment site. For example, the systems and methods may be used to deliver a substance to treat conditions caused by herpes simplex virus infection or to treat clinical conditions suspected to be caused by herpes simplex virus infection. In addition, the systems and methods may be used to treat acne, human papilloma virus and skin wrinkles. Substances generally include natural or homeopathic products that may be outside the definition of medicaments as well as medicaments (e.g., lidocaine for transdermal anesthetization, anti-viral agents for herpes infections, and anti-fungal medicine for athlete's foot such as ketoconazole, nystatin, griseofulin, or flucytosine) and in connection with barriers other than skin (e.g., cell membranes, mucosal membranes, finger or toe nails etc.). By medicament is meant any chemical or biologic that may be used on or administered to humans or animals as an aid in the diagnosis, treatments or prevention of disease or other abnormal or cosmetic condition or for the relief of pain or to control or improve any physiologic or pathologic condition. Additional examples include by way of illustration, not limitation: abacavir, adefovir, amprenavir, azidothymidine, behenyl alcohols, such as n-docosanol, (Abreva), brivudin, cidofovir, delaviridine, didanosine, doxorubican, efavirenz, famciclovir, fluorouracil, (5-FU), gancyclovir, indinavir, terbinafine HCL, (Lamisil), lamivudine, lobucavir, lotrimin, methotrexate, miconazole, (Micatin), nelfinavir, nevirapine, ribavirin, ritonavir, saquinavir, sorivudine, stavudine, tacrolimus, triamcinolone acetonide, trifluridine, valaciclovir, zalcitabine with or without a C21–C28 aliphatic alcohol or in combination thereof. Other examples include anti-virals for treating human papilloma virus (HPV) (e.g., warts (common, flat, plantar and genital)) such as Imiquimod® sold as Aldara™ by 3M for genital warts, Acyclovir®, sodium salicylate, tretinion, benzoyl peroxide, bleomycin, interferons, Podocon-25 and OTC products such as Wart-Off by Pfizer and Compound W by MedTech. Still further examples include anesthetics such as lidocaine, xylocaine, prontocaine, prilocaine, fetanyl, remifentanil, sufentanil, alfentanil, novocaine, procaine, morphine HCL and EMLA either in stand-alone fashion or with a vasodilator such as epinephrine.

The systems and methods may also be used to treat skin discoloration from rosacea, vitiligo and age spots, for example. For rosacea, the systems and methods may be used to deliver drugs such as metronidazole that decrease the presence and proliferation of capillaries in the skin. For vitiligo, the systems and methods may be used to deliver drugs that increase the production and spread of melanin containing skin cells or stimulates production of skin pigmentation. For age spots, the systems and methods may be used to deliver drugs that decrease the pigmentation in age spots on the hands and/or face.

The systems and methods may also be used to provide anti-aging treatments. For example, estrogen or estrogen analogues may be topically delivered to the skin to stimulate estrogen receptors. These substances may be delivered to the face to prevent wrinkles or to the hands to prevent or eliminate age spots. One example treatment for wrinkles is delivering a modulator of collagen deposition such as an organic nitrate (e.g., gallium nitrate).

Acne may be treated using one or more steroids, NSAIDs (non-steroidal anti-inflammatory drugs), such as ketorolac or medicaments such as Benzamycin, benzoyl peroxide, cleocin, T-Stat, over the counter (OTC) products such as Clearasil and Benzac or Accutane, tazarotene sold as Tazorac, adapalene sold as Differin by Allergan and Galderma or azelaic acid, a topical cream also sold by Allergan, erythromycin as well as combinations of such medicaments.

In addition, azelaic acid, clindamycin phosphate (with or without benzoyl peroxide), tretinoin, isotretinoin, tetracycline hydrochloride may be used for acne and furuncles (boils); salicylic acid for HPV (warts); diclofenac sodium for actinic keratosis or contact dermatitis, rash, dry skin and exfoliation; and penciclovir and famciclovir for herpes. Other substances that may be used include corticosteroids such as betamethasone, betamethasone acetate, betamethasone Na phosphate; antimicrobials such as silver sulfadiazine; anti-itch substances such as diphenhydramine; ammonium lactate, hydroquinone, anthralin, caffeine and methyl paraben.

Still other substances that may be used in connection with the systems and methods described herein are identified in application Ser. Nos. 09/523,217; 09/584,138; 10/117,346; and 10/245,337, which are incorporated herein by reference. In addition, the substances described above may be used in the systems and methods described in these other applications.

A system and method for the safe application of an electrokinetic delivery system, such as iontophoresis, is described with reference to FIGS. 2 through 5. The system and method are based on the use of a high frequency rectified current in conjunction with three electrodes, referred to herein as a treatment electrode, a counter electrode and an auxiliary electrode. For purposes of illustration, transdermal delivery of morphine is used as an example.

Figure 2:
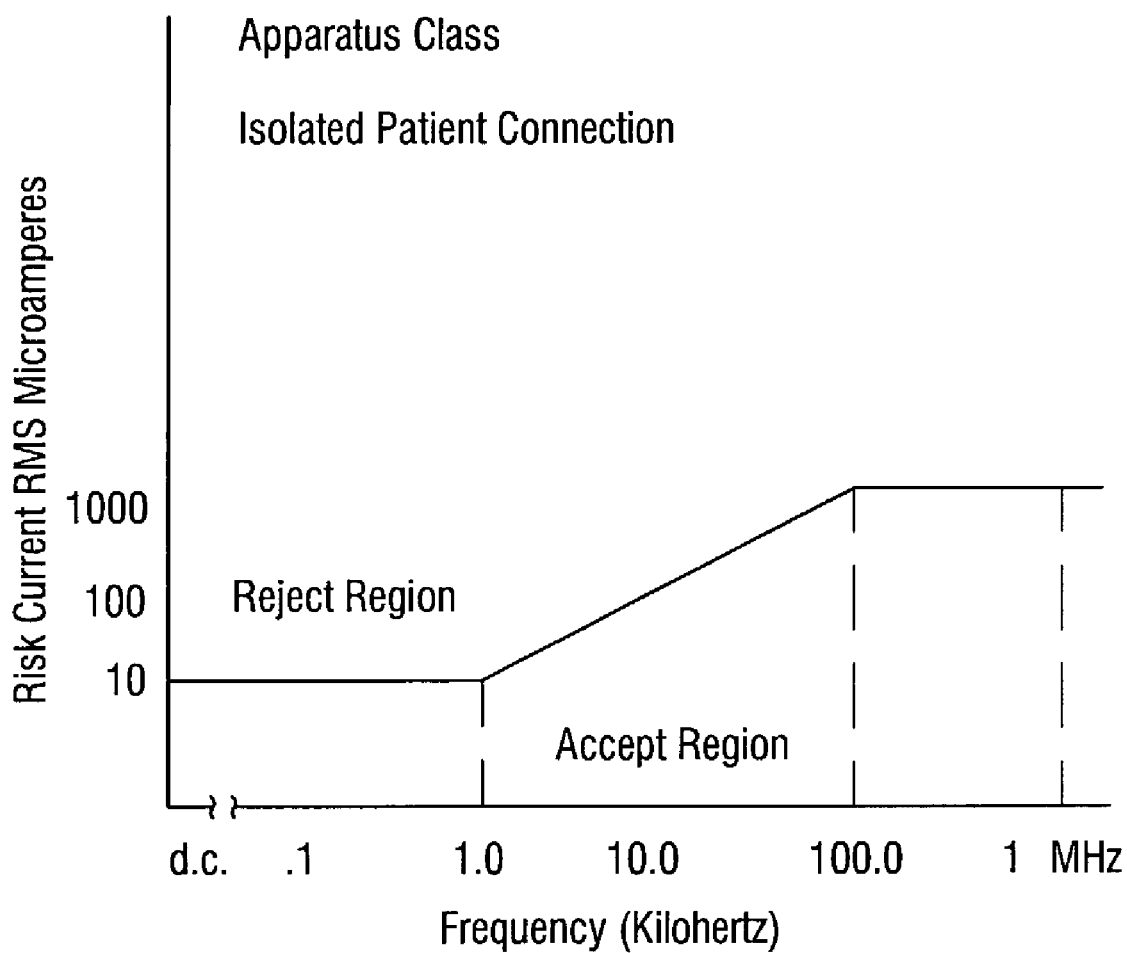
FIG. 2 is a graph of risk current (RMS) in microamperes versus frequency showing the risk current limits based on fibrillatory thresholds.

As described above, iontophoresis involves the use of a current to deliver a substance to tissue. In some conventional systems, depending on usage there is a potential hazard associated with ventricular fibrillation and cardiac arrest if the current generated during iontophoresis accidentally passes through the patient's heart. The standard current threshold for ventricular fibrillation risk increases with frequency. FIG. 2 is a graph of risk current (RMS) in microamperes versus frequency showing the risk current limits based on fibrillatory thresholds. For direct current (DC), the limit is 10 microamperes. For frequencies from 1 kilohertz to 100 kilohertz, the risk current limit varies from 10 microamperes to 1 milliampere. For frequencies above 100 kilohertz, but below 1 megahertz, the risk current limit remains at 1 milliampere. See, for example, AAMI (Association for the Advancement of Medical Instrumentation) Standard, "Safe Current Limits for Electromedical Apparatus."

Figure 3A:
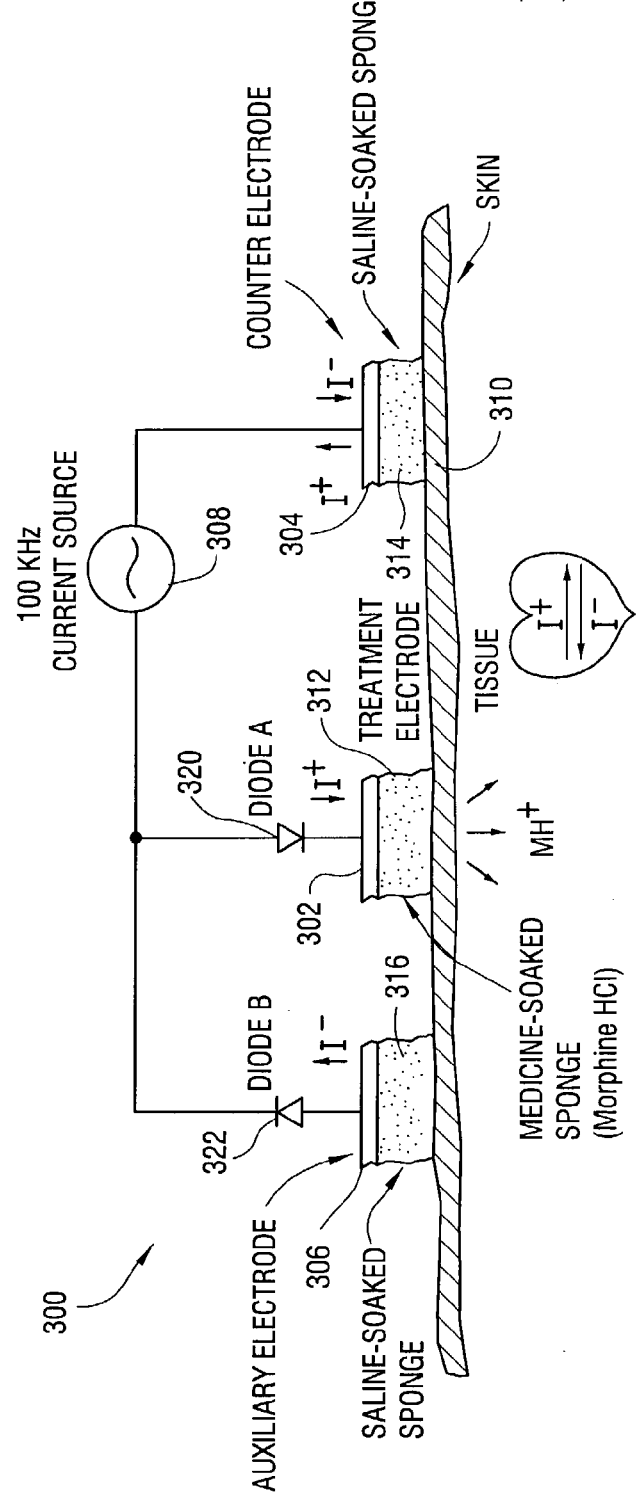
FIG. 3A shows an iontophoretic delivery system 300 in accordance with an embodiment of the present invention.

FIG. 3A shows an iontophoretic delivery system 300 in accordance with an embodiment of the present invention. System 300 includes a treatment electrode 302, a counter electrode 304 and an auxiliary electrode 306 connected to a 100 kilohertz alternating current source 308. Electrodes 302, 304 and 306 are in electrical contact with the patient's skin via conductive layers 312, 314 and 316, respectively. Such layers may, for example, be part of a medicament-carrying substrate or pad. The medicament-carrying substrates or pads are generally disposable and non-reusable and may be releasably adherable to the patient's skin and/or to electrodes 302, 304 and 306. Conductive layer 312 is shown in FIG. 3A as comprising a medicament-soaked sponge or other porous open cellular material, such as cotton, and conductive layers 314 and 316 are shown in FIG. 3A as each comprising a saline-soaked sponge or other such conductive material.

For example, conductive layer 312 may be of a mesh-like construction having vertical cells dimensioned to accommodate a viscous fluid within the confines of the cellular structures. The viscous fluid contained within the plurality of cells includes a medicament that is in a form suitable for transport under the influence of an electric current. Conductive layers 314 and 316 may be mesh-like tactile conductive portions that contain an electrically conductive gel or fluid therewithin. Each of the conductive layers has a lower skin-facing surface and an upper electrode-facing surface. The cells form apertures between the lower skin-facing surface and the upper electrode-facing surface. The device-facing surfaces of the electrodes may further include an adhesive layer applied thereto for suitably releasably adhering the electrodes to the iontophoresis device.

Auxiliary electrode 306 is located lateral to, behind or near treatment electrode 302. Auxiliary electrode 306 and treatment electrode 302 can be in close proximity to each other and the area of auxiliary electrode 306 can be very small compared to the area of treatment electrode 302. These features permit design of a compact hand-held unit in spite of the addition of an auxiliary electrode. In one particular implementation, the total area can be reduced to a minimum by placing auxiliary electrode 306, in the form of a metal mesh, in front of treatment electrode 302. The open mesh allows free passage of medicament and ions to and from treatment electrode 302. Of course, auxiliary electrode 306 may be positioned elsewhere and the present invention is not limited in this respect.

Treatment electrode 302 is connected to AC source 308 via a current path including a first rectifying element 320 for passing current flowing from AC source 308 to skin (and tissue) 310 and blocking current flowing from skin (and tissue) 310 to AC source 308. In the illustrative FIG. 3A embodiment, first rectifying element 320 is a diode having its anode connected to AC source 308 and its cathode connected to treatment electrode 302. Auxiliary electrode 306 is connected to AC source 308 via a current path including a second rectifying element 322 for passing current flowing from skin (and tissue) 310 to AC source 308 and blocking current flowing from AC source 308 to skin (and tissue) 310. In the illustrative FIG. 3A embodiment, second rectifying element 322 is a diode having its anode connected to auxiliary electrode 306 and its cathode connected to AC source 308. Counter electrode 304 is connected to AC source 308 via a bi-directional current path over which current can flow from AC source 308 to skin (and tissue) 310 and from skin (and tissue) 310 to AC source 308. Those skilled in the art will recognize that the rectifying elements in FIG. 3A may be other types of electronic components such as transistors. In use, treatment electrode 302, counter electrode 304, auxiliary electrode 306 are placed in electrical contact with skin 310 via conductive layers 312, 314 and 316, respectively. Conductive layers 312, 314 and 316 may be releasably attached to the electrodes and/or to skin 310 using, for example, a releasable adhesive. Iontophoretic system 300 is then turned on using, for example, a switch (not shown in FIG. 3A). During the positive cycle portions of AC source 308, a component current I+ flows from treatment electrode 302 to the patient's skin and tissue and from the patient's skin and tissue to counter electrode 304. In this way, for example, morphine HCL ions (MH+) are delivered to the tissue covered by the patient's skin. During the negative cycle portions of AC source 308, a component current I− flows from counter electrode 304 to the patient's skin and tissue and from the patient's skin and tissue to auxiliary electrode 306.

Figure 4:
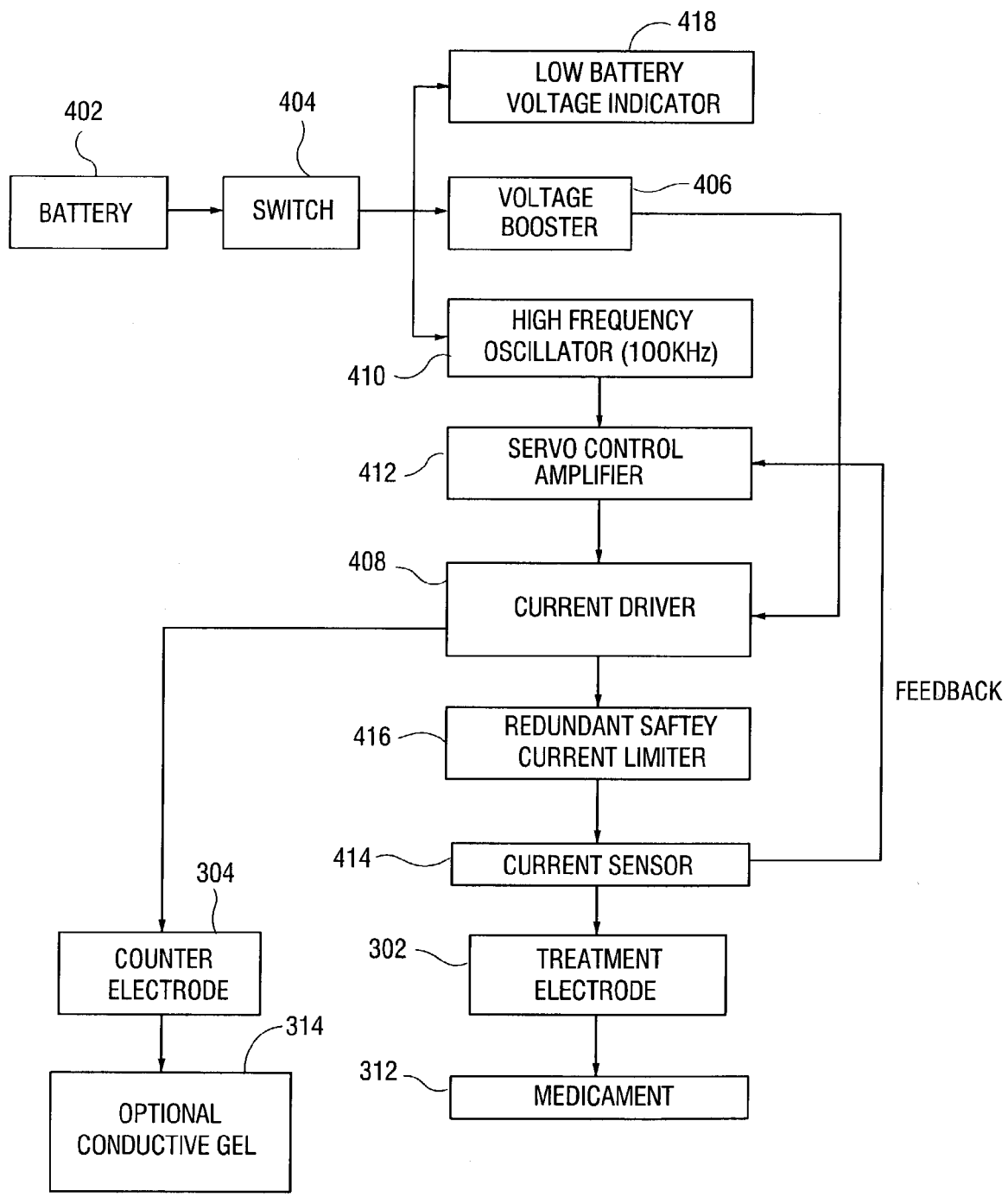
FIG. 4 shows a block diagram of electrical circuit elements of an embodiment of the present invention.

FIG. 4 is a block diagram showing electronic circuit design elements used in an illustrative implementation of a high frequency unidirectional iontophoretic medicator in accordance with an embodiment of the present invention. In this example, power source 402 is a battery comprising one or more AAA-sized primary cells connected either in series or in parallel. Counter electrode 304 is connected to an output of current driver 408 (see FIGS. 4 and 5). An optional conductive layer 314 (such as a conductive gel or a saline-soaked sponge) is used to facilitate current flow to and from the patient's skin. An internal mechanical or electronic switch 404, activated externally by a magnet or magnetic material 520 (see FIG. 5), controls the on and off status of the device. A voltage booster circuit 406 converts the low battery voltage (e.g., 1.5 to 3 VDC) to a high voltage around 30 VDC. The high voltage or high potential is preferred to allow a current driver 408 to overcome any tissue resistance. An oscillator circuit 410 generates a square-wave or sinusoidal AC signal with the selected operating frequency (e.g., 100 kilohertz). A servo-controlled amplifier 412, in synchronization with the oscillator signal, controls the current magnitude based on current feedback signals from a current sensor 414. A current driver stage 408 controls the bias voltage and maintains the desired current to treatment electrode 302. A redundant current limiter 416 is used to provide a safe upper limit for the treatment current. A low battery voltage indicator 418 (e.g., an LED) signals when the battery capacity is low.

Figure 5:
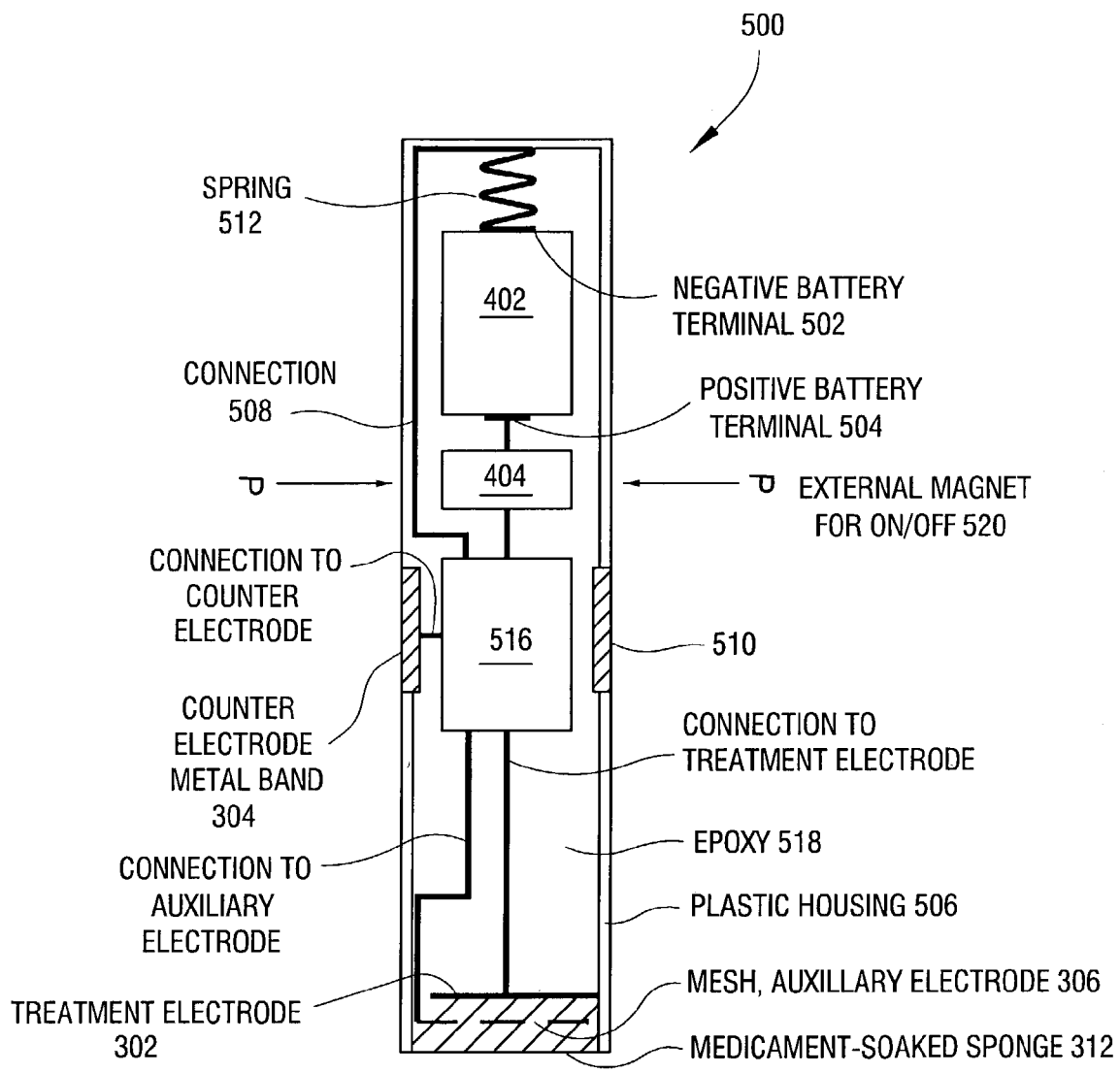
FIG. 5 shows a hand-held device with internal layout of electric and electronic elements.

FIG. 5 illustrates a hand-held device 500 into which the various circuit elements of FIG. 4 may be incorporated. Of course, it will be apparent that the circuit elements of FIG. 4 may be incorporated in a wide variety of devices and the device of FIG. 5 is provided by way of illustration, not limitation. The hand-held device shown in FIG. 5 is configured along the lines of the hand-held devices shown in U.S. Pat. Nos. 5,676,648, 5,879,323 and RE37,796, the contents of each of which are incorporated herein by reference. For ease of illustration, not all of the elements shown in FIG. 4 are shown in FIG. 5. Housing 506 of the handheld device is preferably formed of plastic and is shaped to comfortably fit within a user's hand. Medicament-soaked sponge 312 is in electrical contact with treatment electrode 302. A mesh or gridded auxiliary electrode 306 is, as an example, interposed between treatment electrode 302 and the patient. Negative battery terminal 502 is connected via an electrical connection 508 to an electronic package 516, and an output of a current drive circuit within electronic package 516 connects to counter electrode 304 provided as a metal band 510 circumferentially (either continuously or discontinuously) formed around housing 506. For the self-administration of medicament, a user touches counter electrode 304 with his/her skin (e.g., fingers). Electrical connection 508 includes a spring portion 512 for holding power source (battery) 402 in place. Positive battery terminal 504 is connected to switch 404 (e.g., a mechanical reed switch or an electronic switch activated by an external magnet denoted at 520). Element 516 in FIG. 5 designates an electronic package at least containing oscillator 410, amplifier 412, current driver 408, redundant safety current limiter 416, current sensor 414 and rectifying elements 320 and 322. Some or all of the components within housing 506 may be contained in epoxy 518.

With conventional equipment, the portion of the current possibly directly traversing the patient's heart could reach a level resulting in ventricular fibrillation. In accordance with the above-described embodiment of the present invention, the frequency of the electrical driving circuit is increased from 0 (DC) to 100 kilohertz. As can be seen with reference to FIG. 2, in this case, the current can be safely increased up to 1 milliampere (RMS). This results in effective delivery of the medicament to the patient. Thus, the use of rectified high-frequency iontophoresis as described above satisfies the established risk-current limit requirements and eliminates the hazard of ventricular fibrillation. In addition, the goal of unidirectional iontophoresis like that of the DC approach can be obtained. Therefore, although the AC current is rectified at the treatment site to obtain DC-like, unidirectional iontophoresis, any current passing through the heart remains strictly bi-directional and alternating with a frequency high enough to satisfy the risk(leakage) current requirement.

In rare cases in which AC iontophoresis is applicable, the hazard associated with ventricular fibrillation can also be eliminated by using a high frequency current source around 100 kilohertz. In this special case, rectifying elements and auxiliary electrode 102 are not required because AC iontophoresis is desired. The same circuit design used for unidirectional AC electrophoresis (FIG. 4) is directly applicable.

In some applications, the afflicted or desired treatment area may become relatively large (e.g., greater than approximately 2 square centimeters). Examples of such applications may include some acne cases; treatment with antibiotics/anti-inflammatory medicines; athlete's foot and nail bed onychomycosis with anti-fungal agents; large area facial anesthetization with anesthesia (e.g., lidocaine) prior to injection of botulinum toxin A (commercially available as BOTOX®) for cosmetic remedy; and others. BOTOX is a registered trademark of Allergan, Inc. For a large area treatment, it is desirable to increase both the rectified current and the area of the treatment electrode. The transfer of substance per unit area can remain the same if the total current increases in proportion to the area such that the current density (current per unit area) remains unchanged. As both the current and the electrode area increases, there is a greater tendency for the current to concentrate to a small area of the electrode surface due to uneven pressure being applied to the larger electrode. For total current greater than approximately 400 microamps or electrode area in excess of 2 square centimeters, current concentration becomes a serious safety concern. It can lead to severe burn, skin and tissue damage as well as non-uniform delivery of medicament.

Figure 3B:
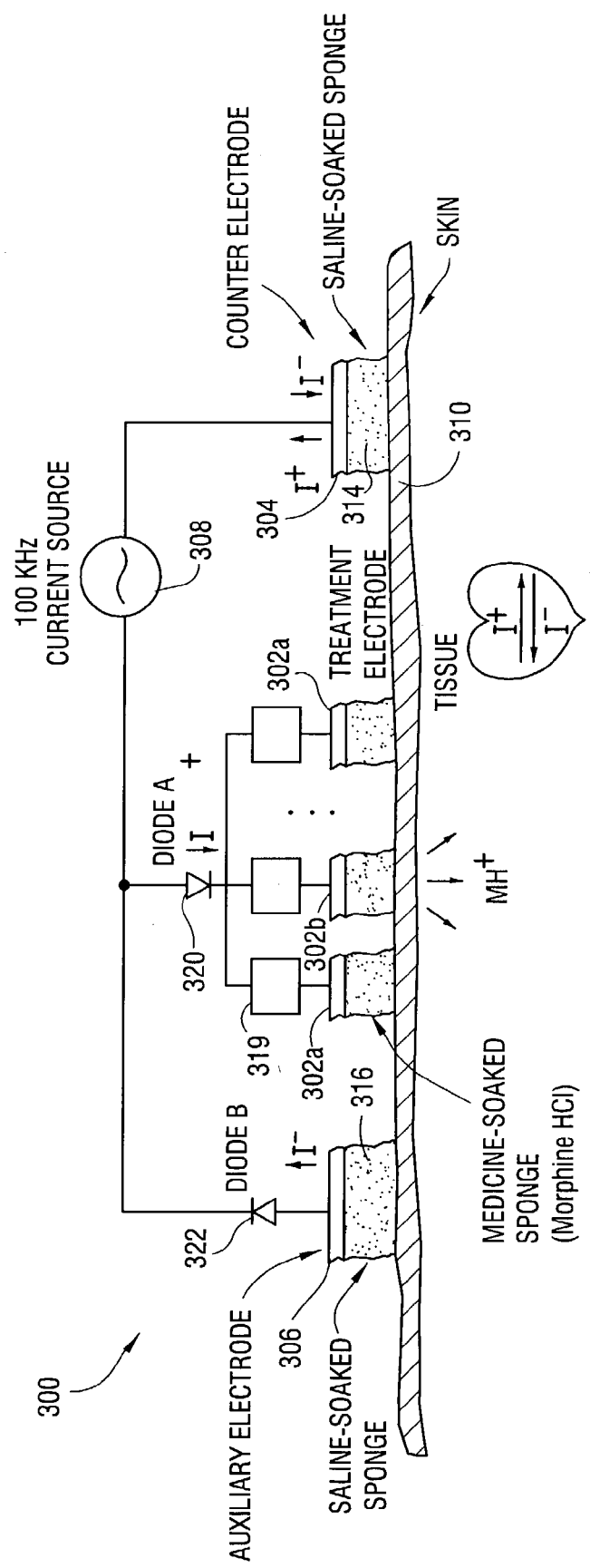
FIG. 3B shows an iontophoretic delivery system 300' in accordance with another embodiment of the present invention.

For large electrode area, the treatment electrode 302 in FIG. 3A can be sub-divided into a multitude of small electrodes 302a–302n rectified by the same diode 320 as shown in FIG. 3B. Current-limiter devices 319, serving as a current-partitioner, can then be inserted between diode 320 and each sub-divided electrode. The substantially increased total treatment current I+ (for large area treatment) illustrated in FIG. 3A can thus be partitioned into smaller current components flowing through each sub-divided electrode. Due to the insertion of a current-limiter, the current flowing through each sub-divided electrode is identical, limited, and cannot exceed the partitioned value. The hazard associated with current concentration can thus be averted completely. The current-limiter is preferably an active device (such as a current diode LM334 manufactured by National Semiconductor Corp. and Linear Technology Corp.) or simply, a resistor. A similar technique can also readily be applied to the auxiliary and the counter electrode for alleviation of current concentration. Although FIG. 3B shows each sub-divided electrode 302a–302n associated with a corresponding conductive layer, the invention is not limited in this respect in that a one conductive layer may be associated with two or more or all of the sub-divided electrodes.

Additional embodiments of an electrokinetic device will now be described. These embodiments use a printed circuit board (PCB) with a substance-filled porous matrix on one side and a conducting hydrogel on the opposite side. The matrix is in contact with a treatment (active or applicator) electrode on the PCB beneath the matrix. The electrically conducting hydrogel is in contact with a circumferential-ring counter electrode provided on the opposite side of the PCB as the treatment electrode. In use, the treatment current circulates from the treatment electrode through matrix into the skin and tissue, through the arm and finger back into counter electrode to complete the circuit.

One embodiment adaptable for large treatment areas (but not limited thereto) utilizes a simple, low-cost, electrokinetic, stacked patch medicator built with discrete components on a PCB. The small and lightweight patch is attached to the user's fingertip via a layer of suitably sticky, electrically conducting hydrogel and can, for example, be applied to the face in a highly maneuverable and effortless manner. The patch medicator facilitates the delivery of a medicament to a diseased subcutaneous tissue by injecting a controlled current through the medicament (that may, for example, be contained in a reservoir) through the skin, the underlying layers and ultimately, to the treatment site (the basal epidermis, for instance). An example design uses only low-cost, compact, lightweight, surface-mount and die components and one or more small coin cell batteries as a power source. The patch medicator includes a low-power microprocessor/microcontroller providing servo control, timing management, current measurement, hardware monitoring, circuit interface and outputs for visual indication.

With reference to FIGS. 6A–6C, the patch medicator 600 is built on a small gold-plated PCB 602 with a substance-filled porous matrix 604 on one side and a conducting hydrogel 606 on the opposite side. The matrix is surrounded by an insulator, e.g., a rubber or plastic retaining ring 608 on its perimeter and is in contact with a gold-plated treatment (active or applicator) electrode 610 on PCB 602 beneath the matrix. The electrically conducting hydrogel 606 is in contact with a gold-plated, circumferential-ring counter electrode 611 provided on the opposite side of PCB 602 as treatment electrode 610. Although the hydrogel layer 606 may cover the entire area of PCB 602, it is constructed so that it has a built-in cavity where circuit components 612 and battery 614, embedded in an insulator such as rubber epoxy 613, are installed. In use, the treatment current circulates from the treatment electrode 610 through matrix 604 into the skin and tissue, through the arm and finger back into counter electrode 611 to complete the circuit. An on/off switch 616 can simply be a tiny, inexpensive jumper connector or a thin insulating plastic strip pulled off by the patient prior to treatment. A heat sealable aluminum foil cover (not shown) provides protection from degradation of the matrix 604 in storage. Similar protection for the hydrogel 606 can also be used. The diameter of the patch medicator can be reduced to less than 15 mm, if desired. While the medicament is described above as being in a porous matrix, the matrix is optional or, if provided, the matrix may not be porous (e.g., substance in hydrogel or gel emulsion). LED indicator(s) 626 provide status information to the user.

The patch medicator 600 is usable with the substances and for the treatments described in detail above. In one specific use, particularly for the treatment of Herpes I and II-type infections, Acyclovir® is the medicament of choice. Acyclovir® may be provided in a cream formulation with approximately 5% comprising the drug Acyclovir®. For example, a 250 milligram formulation of topical cream containing 12.5 milligrams of Acyclovir®, i.e., a 5% formulation, may be utilized. Significantly, this relatively small amount of medicament in the formulation, when applied electrokinetically over a predetermined time duration, affords a therapeutically effective dose. The dosage and time of application may be varied. For example, an approximate 2% formulation of about 4 to 5 milligrams of the active medicament (e.g., Acyclovir®) in a 250 milligram cream formulation applied electrokinetically over a period of no greater than fifteen minutes or an approximate 14–15% formulation, e.g., 37 milligrams in a 250 milligram cream and Acyclovir® formulation, applied electrokinetically for approximately three minutes is believed therapeutically effective. Percentage formulations between 2%–15% over time durations between fifteen minutes and three minutes are believed also to be therapeutically effective. For example, 8%–10% formulations over 5–6 minutes' time duration are also believed therapeutically effective. Of course, there may be instances where a low percentage formulation may be therapeutically effective even if applied for only a relatively short time at current density approximately equal to, greater than or less than 200 microamps per square centimeter. While a cream formulation is preferred, it will be appreciated that the topical base may also be a liquid, gel, ointment or lotion.

The patch medicator may be designed for limited use such as a single use. The medicator patch may be disposable or for more than one use if the substance matrix is designed to be replaceable by the patient using the patch. The hardware component count of the patch may be minimized with more elaborate software implementation and large integrated circuits (ICs) may be used in the die form to reduce size and weight. Finally, the patch is designed to use miniature watch or hearing aid battery as a power source.

Figure 7:
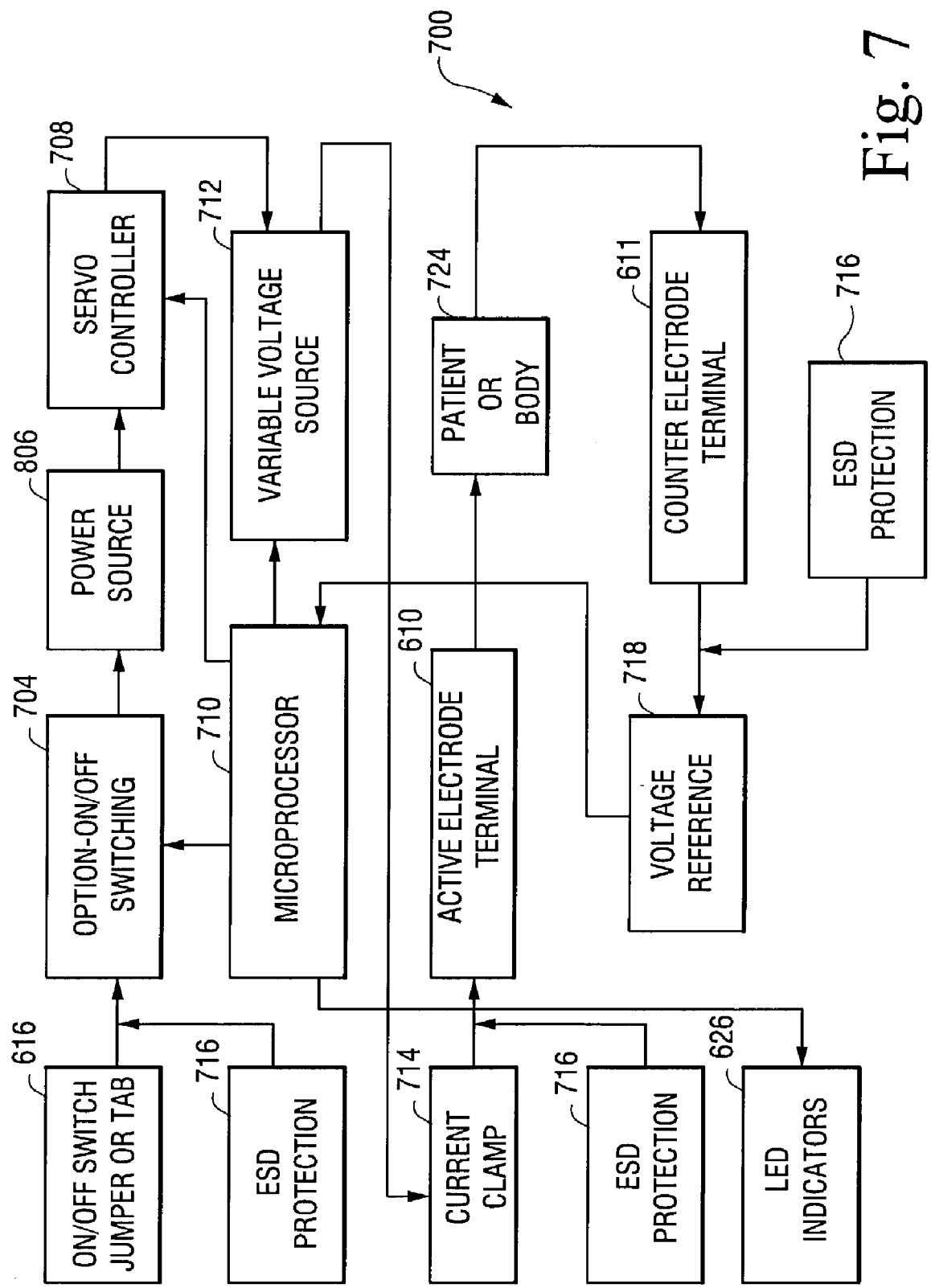
FIG. 7 is block circuit diagram of the electrical elements of the patch medicator of FIGS. 6A–6C.

FIG. 7 is block circuit diagram of example electrical circuitry 700 that may be used to provide the patch medicator of FIGS. 6A–6C for use by a patient 724. Electrical circuitry 700 includes an on/off switch 616; an (optional) power on/off switch 704; a power source 706; a servo controller 708; a microprocessor/microcontroller 710 (hereinafter microprocessor 710); a variable voltage source 712; a current clamp 714; electrostatic discharge (ESD) protection circuits 716; a voltage reference 718; counter electrode terminal 611; treatment (active or applicator) electrode terminal 610; and LED indicator(s) 626.

On/off switch 616 is implemented, for example, by a shorting jumper or a plastic film tab. A pressure sensitive switch may also be used. This switch serves as a power-on switch for the patch medicator. Optional power on/off switch 704 may be provided if the device is intended for more than one use. In this case, a power switch such as a semiconductor power switch is used to power off the device after each use. Power source 706 is two miniature and thin watch batteries, connected in series that provide the power for the device. Skin resistance largely determines the bias potential required for sustaining the treatment current. Servo controller 708 maintains a desired current by controlling the treatment potential generated by the variable voltage source 712. Variable voltage source 712 generates the treatment potential by converting a low supply voltage (2 to 3 V) to a variable output voltage of up to 34 V. Although the treatment current is maintained by feedback control, a redundant current clamp 714 is used to limit the current to a safe upper limit in order to safeguard against servo loop malfunction. A constant voltage source 718 is used as a stable reference standard for treatment current and for analog-to-digital conversion. ESD protection circuits 716 are transient voltage suppressors that protect circuit elements from ESD damage. LED indicator(s) 626 are used to indicate various treatment stages and to display warning signals. The LEDs may be used in a miniature surface mount package or in die form and are placed strategically to be visible to the patient in direct view or via reflection off nearby surfaces. For example, LED indicator(s) 626 may be a bi-polar red and green LED. Under some conditions, the red and green LEDs may be illuminated simultaneously to create an amber color. Both function blocks, the servo controller and the variable voltage source, may be composed merely of simple active and passive building blocks such as transistor, diode, capacitor and inductor driven by feedback control software executed by microprocessor 710.

Microprocessor 710 controls the overall operation of the patch medicator. Although the example implementation described herein uses a microprocessor/microcontroller, the invention is not limited in this respect and other types of processing circuitry such as digital signal processors, application specific integrated circuits (ASICs), programmable logic arrays or some combination thereof may also be used. An example microprocessor/microcontroller is the Microchip Technology PIC16LF872. If this microcontroller is used, the software may be written in assembly language and an assembler such as MPASM™ may be used. Microprocessor 710 includes (or has access to) read-only memory (e.g., for storing code) and/or read/write memory (e.g., for storing data). In the example implementation, microprocessor 710 includes a non-volatile read/write data memory such as an EEPROM. The operations of microprocessor 710 are implemented in software. Data and instructions for controlling the overall operation of the patch medicator may be written respectively to EEPROM data memory and Flash program memory, and microprocessor 710 may execute the instructions in response to various signals supplied thereto. These instructions may include instructions for:

monitoring the treatment current and the battery terminal voltage;
  controlling the slow rise and fall of the treatment current ("ramping") to minimize the uncomfortable sensation of current flow;
  timing control of treatment period and automatic treatment termination;
  illumination of LEDs for treatment status indication;
  monitoring treatment history and controlling the frequency of use and de-activation of the device after the prescribed usage is exhausted;
  performing self-diagnosis and self-consistency checks;
  monitoring the proper operation of other circuit components;
  controlling and minimizing the current drain of LEDs based on battery voltage measurements; and
  monitoring treatment process and current control to accommodate fidgety patients as well as treatment interruptions.

FIGS. 8A and 8B illustrate an example system state table showing the states of the patch medicator and the conditions and responses that occur in each. Of course, the states described in this state table may be implemented in other electrokinetic devices described herein and in the applications incorporated herein.

After power is turned on, an initialization process may be performed. During initialization, the software initializes the hardware registers and the microprocessor is initialized. During microprocessor initialization, registers, ports, interrupts, handlers, timers, A/D converters and the watchdog timer are set up. An interruption count indicative of the number of interruptions (i.e., a user-caused discontinuity in the current path during treatment that lasts longer than a predetermined period of time such as two seconds) is reset. After initialization and prior to treatment, patch medicator 600 performs certain self-diagnostic tests (referred to in FIGS. 8A and 8B as POST test(s)). These tests include, for example, a low-battery check and a general electronics test (e.g., program memory check, data memory check, A/D converter check, etc.). Microprocessor 710 controls LED indicators 626 (e.g., by flashing the green status LED) to inform the user that the self-diagnostic test is being conducted. In the event that a self-diagnostic test fails, microprocessor 710 of the patch medicator inhibits further operation and informs the user of the failure by, for example, flashing a red status LED.

Following the self-diagnostic test, the device enters the READY state in which microprocessor 710 begins to periodically monitor (e.g., every 100 milliseconds) the current applied to the electrodes. If there is excessive idle time as determined with reference to the READY timer (i.e., user does not initiate treatment within some predetermined time after successful completion of the self-diagnostic test such that the measured current is zero (or less than a threshold value such as 10 microamps), microprocessor 710 puts the device in the OFF state. Microprocessor 710 may also check a TREATMENT counter to determine the number of treatments for which the device has been used. If the device has already been used for the pre-programmed number of treatments, the device enters an ERROR state, which turns the device off. If the treatment counter is not exceeded, the device remains in a READY state until current flow is sensed. At this point, the device proceeds to a RAMP-UP state in which microprocessor 710 increments the TREATMENT counter and ramps up the current delivered to the electrodes from zero to an appropriate therapeutic current. The therapeutic current is a treatment current range for application effectiveness and determining the duration of the treatment. The current is applied between the treatment electrode and the counter electrode for the purpose of delivering medicament to a treatment site. The green status LED may be flashed to provide an indication to the user that the current is ramping up. Once the current across the electrodes reaches the treatment current threshold, the device enters the TREATMENT state in which microprocessor 710 starts the TREATMENT timer and continuously illuminates green status LED to indicate to the user that medication is being actively delivered. During the TREATMENT state, microprocessor 710 maintains treatment current and monitors for interrupts, faults and low-battery conditions. If desired for a particular treatment type, the treatment current may be pulsed.

Microprocessor 710 automatically ends each treatment after the treatment current has been applied to the electrodes for an appropriate treatment time. To end a treatment, microprocessor 710 ramps down the current delivered to the electrodes from the treatment current to zero. When the current falls to a termination level, microprocessor 710 extinguishes the green status LED and continuously illuminates the amber LED.

In the event that treatment is interrupted by the user prior to reaching the predetermined treatment time, the INTERRUPT counter is incremented and an INTERRUPT timer is started. If the INTERRUPT counter exceeds a predetermined count or the INTERRUPT timer exceeds a certain time, the device goes to a T-FAULT state in which the current is set to (or maintained at) zero and the device enters a LOCKOUT state in which the user cannot use the device again for a predetermined period of time. If the interruption is only temporary, only the timer is paused and the treatment is resumed after the temporary interruption by ramping the current up to the treatment current value like at the beginning of the treatment. During an interruption, the treatment electrode may be discharged to prevent the user from feeling a shock on reapplying the device after removing it.

If certain error conditions are detected after the power is turned on, the software executes error routines that extinguish the green LED, flash the red LED for approximately one minute, and then switch the device off. Examples of these error conditions include a failure(s) in the initialization or diagnostic tests; activation of a watchdog timer; low battery level; treatment counter limit has been reached; and excessive idle time. If during the above-described operations, the battery level falls below a minimal level needed for operation, a counter in non-volatile memory is incremented to track the number of times the level has fallen below this minimal level; the A/D converter is turned off; the treatment current is ramped down; and the error routines are executed.

Microprocessor 710 may include a watchdog timer to reset the processor in the event of some malfunction. If the watchdog timer has been activated, the software terminates operation similarly to the steps described above with respect to low-battery level except that a counter in non-volatile memory indicative of the number of watchdog timer activations is incremented.

By way of illustration, the initiation current may be 10 microamps, the treatment current may be 400 microamps ±8%; the termination current may be 50 microamps ±5%; the nominal current density may be 200 microamps per square centimeter; the current up-ramp and down-ramp timing may be exponential with a approximately a 10-second time constant; the voltage between the treatment and counter electrodes may be from 0 to 34 VDC; and the automatic shut-off period may be after a ten-minute sustained treatment (in the event the treatment is interrupted, the microprocessor will end treatment no later than around eleven minutes after the initial start of the treatment).

To use the patch medicator, the patient removes any cover(s) providing protection of matrix 604 and/or hydrogel 606 and actuates on/off switch 616 to activate the patch medicator on. The patch is then attached to the user's fingertip via the sticky hydrogel and the matrix is applied to a treatment site such as a treatment site on the face. The treatment current of the patch medicator flows from the treatment electrode 610 through matrix 604 into the skin and tissue, through the arm and finger back into counter electrode 611 to complete the circuit. This current facilitates the penetration of medicament through skin and into the diseased subcutaneous tissue. After use, the patient may actuate the power on/off switch 704 to turn off the patch medicator if the patch medicator is intended for multiple uses. The patient may also dispose of the used matrix. To re-use the patch medicator, a new matrix is provided and the patient then actuates power on/off switch to turn the patch medicator on.

The data stored by the read/write memory within (or accessible to) microprocessor 710 may also include a count indicative of the number of treatment cycles for which the patch medicator has been used. This count is incremented (or decremented) for each treatment and the patch medicator is permanently deactivated after the count reaches a prescribed number indicative of a predetermined number of treatments. For example, a disable flag for disabling microprocessor 710 may be set in memory when the count on the counter is indicative of the prescribed number of treatments. Alternatively or additionally, various mechanisms for preventing the supply of power to the electrical components may be used to permanently deactivate the device. For example, microprocessor 710 could generate a signal to burn a fuse when the count on the counter is indicative of the prescribed number of treatments. Similarly, microprocessor 710 could generate a signal to deliberately damage a transistor or flip a solid-state toggle circuit when the count on the counter is indicative of the prescribed number of treatments. It will be readily apparent that other mechanisms (hardware and/or software) may be used and the invention is not limited in this respect.

In another example implementation, the read/write memory may store a total treatment time, which is incremented (or decremented) in accordance with a timer during treatment. When the total treatment time reaches some prescribed total treatment time, the device may be permanently deactivated. Here again, for example, the various hardware and/or software disabling mechanisms described above may be used to permanently deactivate the device.

As mentioned above, the patch medicator may be disabled from use for a predetermined time period (LOCKOUT) after each use whereby the next use can only occur after the predetermined time period has expired. In this case, a disable flag could be set for the predetermined time period and microprocessor 710 could prevent operation of the patch medicator when this flag is set.

Also, the patch medicator may be deactivated permanently after a single usage. Here again, various mechanisms for prevention of re-use of the patch medicator may be used. For example, microprocessor 710 could generate a signal to burn a fuse incorporated in the electric circuitry at the end of a treatment. Similarly, microprocessor 710 could generate a signal to deliberately damage a transistor or flip a solid-state toggle circuit incorporated in the electric circuitry at the end of a treatment. It will be readily apparent that other mechanisms (hardware and/or software) may be used and the invention is not limited in this respect.

Microprocessor 710 may be programmed with (or have accessible thereto) instructions for a plurality of different types of treatments (e.g., herpes, eczema, acne, boils, blemishes and the like). For example, the desired treatment current, ramp-up/ramp down characteristics and total treatment time for herpes may be different than the desired treatment current, ramp-up/ramp-down characteristics and total treatment time for eczema. To determine which instructions to use, the patch medicator may, for example, be provided with a plurality of different on/off switches, each of which is associated with a particular treatment type. Detection by the microprocessor 710 of which on/off switch is activated is used to determine which treatment type is used. Thereafter, microprocessor 710 executes instructions appropriate for the particular treatment type selected.

Assuming appropriate power is available, the patch medicator may be provided with additional elements. For example, sound or vibration generating circuitry such as a buzzer may also be added to provide aural or tactile indications such as warnings, end-of-treatment, etc. Short periodic sound or vibration could indicate the device is continuing to function properly.

Figure 9A:
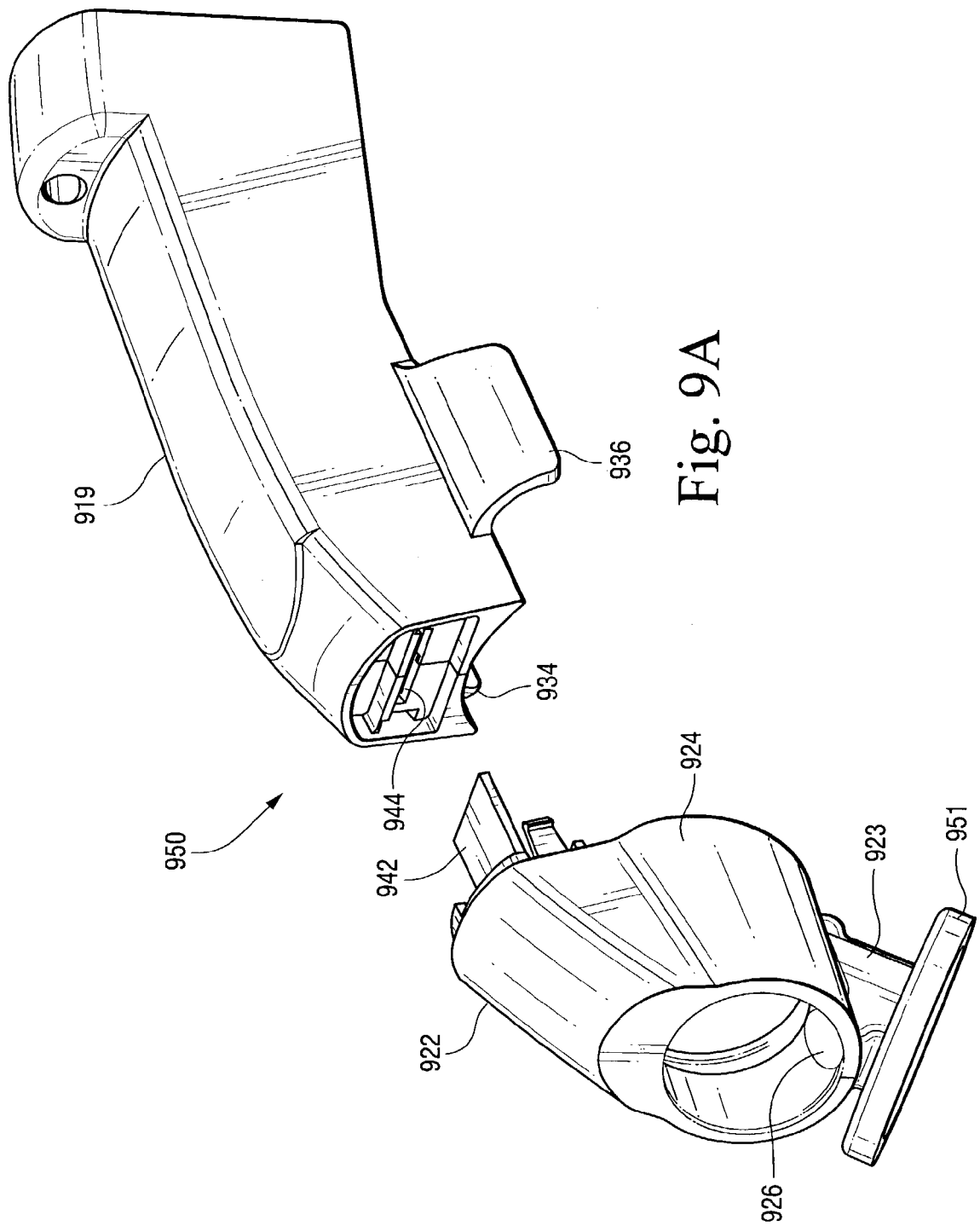
FIGS. 9A and 9B show another PCB device for electrokinetic delivery of a substance.
Figure 9B:
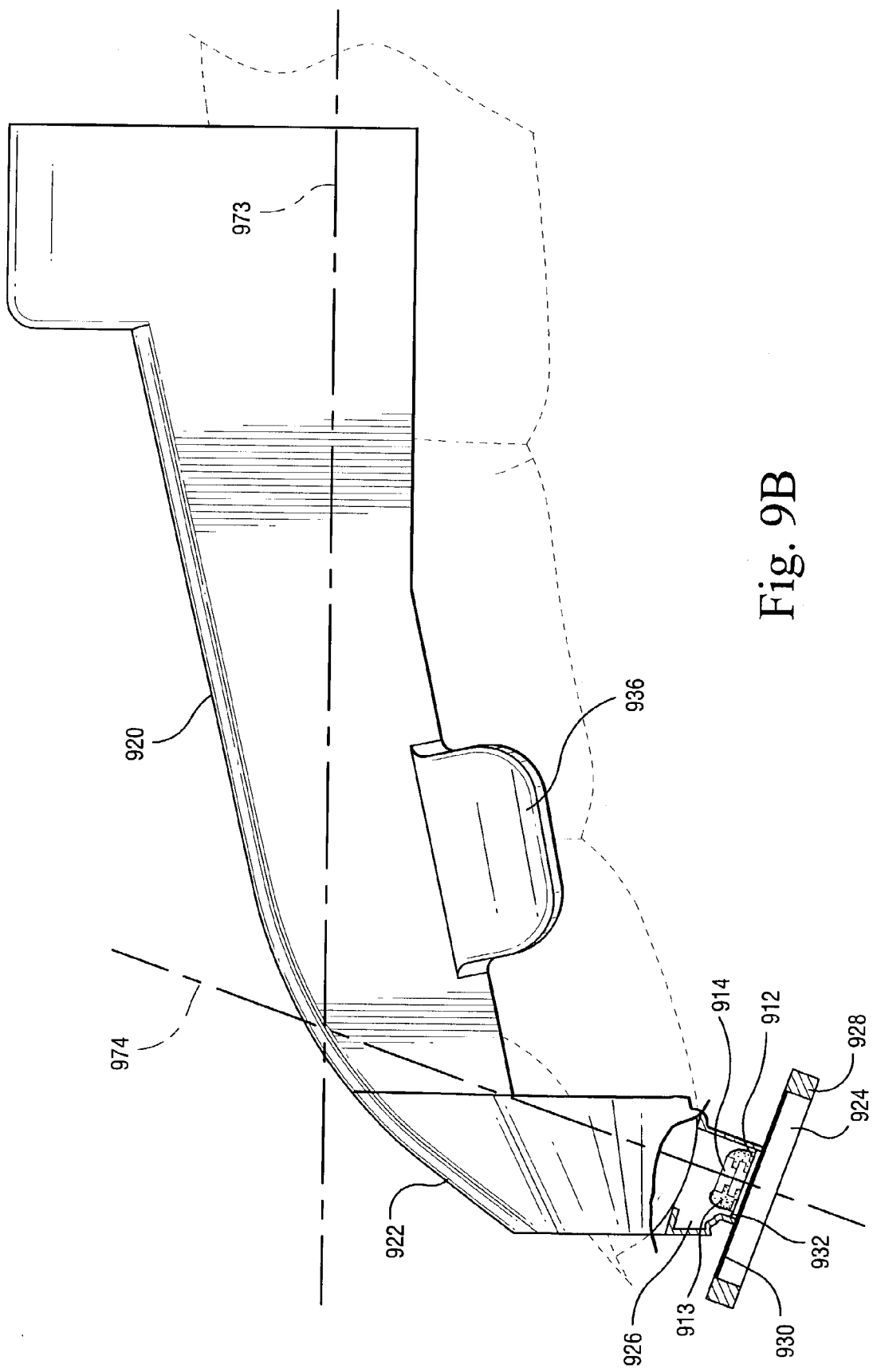

While the PCB arrangement and the features and characteristics thereof have been discussed with reference to a patch medicator, as noted above, this arrangement and the same features and characteristics may be implemented in the devices shown in application Ser. Nos. 09/523,217; 09/584,138; 10/117,346; and 10/245,337, in particular the finger-splint device shown in application Ser. No. 10/117,346. With reference to FIGS. 9A and 9B, the finger-splint device 950 includes proximal and distal portions 919 and 922, respectively, and contacts 942 and 944 in the distal and proximal portions, respectively, for completing the electrical circuit as described herein. The proximal portion 919 includes loops 934 and tabs 936 on opposite sides for securing a strap to the proximal portion and securement of the device to the individual's finger. The proximal portion 919 houses the electronics, which include a PCB 920 with a substance-filled porous matrix 924 on one side and a conducting hydrogel 926 on the opposite side. The matrix 924 is surrounded by an insulator, e.g., a rubber or plastic retaining ring 928 on its perimeter and is in contact with a gold-plated treatment (active or applicator) electrode 930 on the PCB beneath the matrix. The electrically conducting hydrogel is in contact with a circumferential-ring counter electrode 932 on the opposite side of the PCB as the treatment electrode. Although the hydrogel layer may cover the entire area of the PCB, it is constructed so that it has a built-in cavity where circuit components 912 and a battery 914, embedded in an insulator 913 such as rubber epoxy, are installed. In use, the treatment current circulates from the treatment electrode through matrix into the skin and tissue, through the arm and finger back into the counter electrode to complete the circuit. A heat sealable aluminum foil cover (not shown) provides protection from degradation of the matrix in storage. Similar protection for the hydrogel can also be used. The distal portion 922 is generally frustoconically shaped and mounts a pylon or a pair of pylons 923 interconnecting the frustoconical section 924 and the applicator head 951. It will be appreciated that the undersurface of the proximal portion 919 is concave and angled to accommodate the first finger joint and opposite sides thereof for mounting the proximal portion on the individual's finger. Similarly, the distal portion 922 has a frustoconical interior surface for receiving the fingertip of the individual upon electrical and mechanical connection of the proximal and distal portions to one another. In FIG. 9B, the device is illustrated in an operable condition applied to an individual's finger, with the individual's fingertip projecting into the distal portion and in electrical contact with the hydrogel. In the FIG. 9 embodiment, the angle at an intersection between the direction of elongation (centerline 973) and a line 974 perpendicular to the planar surface of the treatment electrode is an obtuse angle of in a range of about 90°–185°, preferably within a range of about 130°–160°. Of course, these ranges are provided merely as examples and the angular direction of the treatment electrode relative to the device is most desirably determined to be whatever angle facilitates application of the device to treatment sites variously located about an individual's body.

Figure 10:
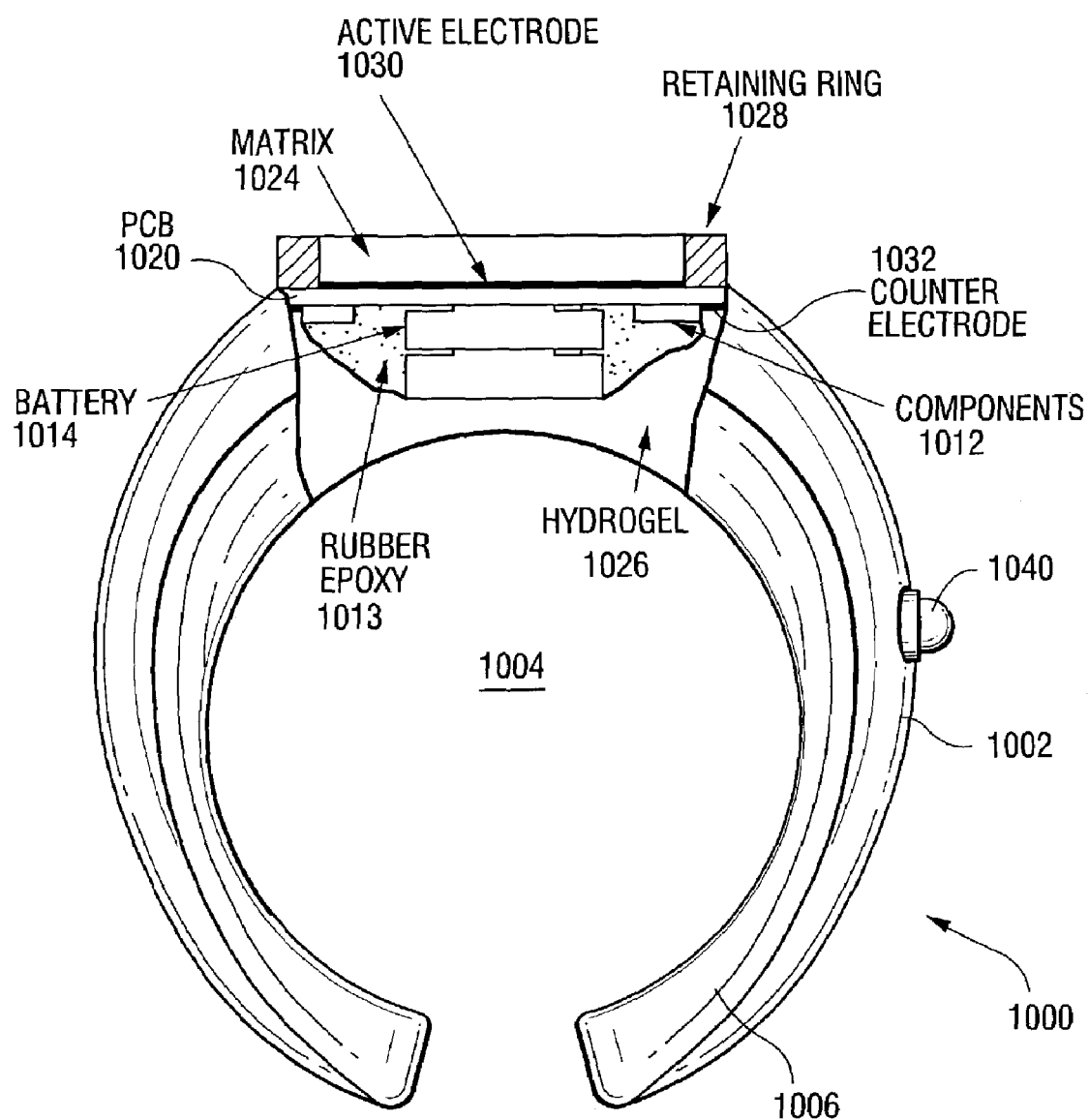
FIG. 10 is a finger-ring mounted PCB device for electrokinetic delivery of a substance.

Similarly, the PCB arrangement may be applied to the finger-mounted electrokinetic device shown in FIG. 10, generally designated at 1000. Device 1000 is generally in the form of a ring carried by or applied about an individual's finger such as the index finger. The generally ring-shaped body 1002 has a through-opening 1004 to receive the individual's finger and which opening is flanked by a pair of arcuate sections 1006 which, together with a top portion of body 1002, form a split ring for maintaining the device 1000 on the individual's finger. It will be appreciated of course that body 1002 may comprise a full circular ring without interruption, although the split ring form provides flexibility in accommodating different finger sizes.

The device 1002 is self-contained and thus includes within its body a small gold-plated printed circuit board (PCB) 1020 with a substance-filled porous matrix 1024 on one side and a conducting hydrogel 1026 on the opposite side. The matrix is surrounded by a rubber or plastic retaining ring 1028 on its perimeter and is in contact with a gold-plated treatment electrode 1030 on PCB 1020. The electrically conducting hydrogel 1026 is in contact with a gold-plated counter electrode 1032 on the opposite side. The hydrogel layer is constructed so that it has a built-in cavity where circuit components 1012 and a battery 1014, embedded in an insulator 1013 such as rubber epoxy, are installed. In use, the treatment current circulates from the treatment electrode 1030 through substance matrix 1024 into the skin and tissue, through the arm and finger back into counter electrode 1032 to complete the circuit. It will be appreciated that upon applying the ring-shaped body 1002 to the individual's finger, the conducting hydrogel will automatically lie in electrical contact with the individual's finger. That is, the flexible side sections 1006 of the device 1000 bias the body 1002 such that the hydrogel is pressed against the individual's finger. As illustrated in FIG. 10, one or more LED's 1040 may be provided to provide on/off indications and the like.

Figure 11A:
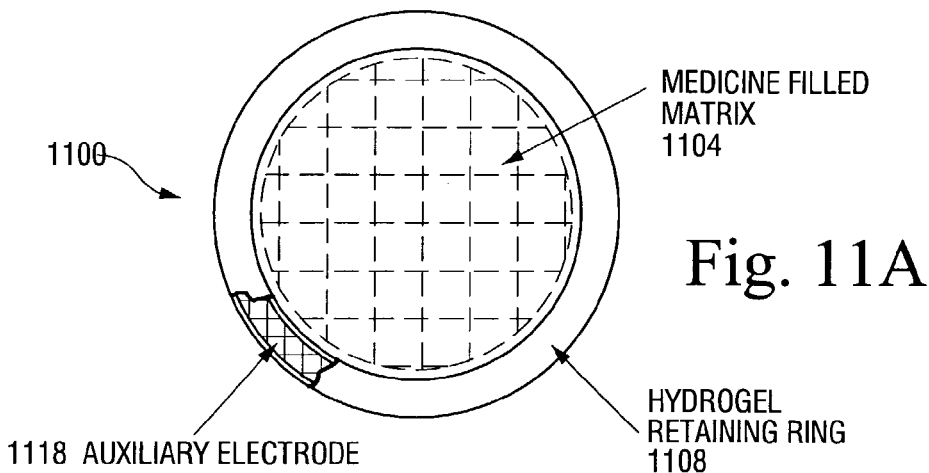
FIGS. 11A–11C are top plan, cross-sectional, and bottom plan views of a PCB patch medicator encompassing features of devices of FIGS. 3A and 3B.
Figure 11B:
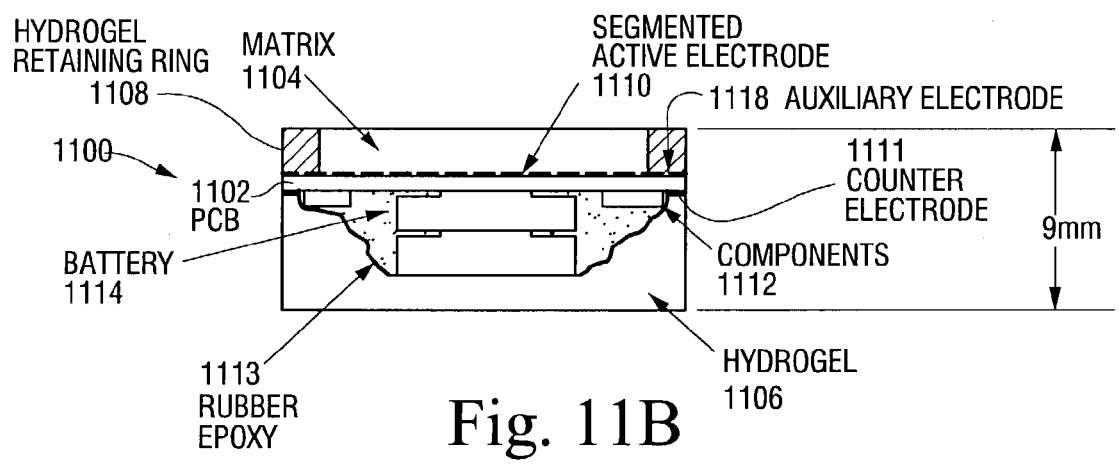
Figure 11C:
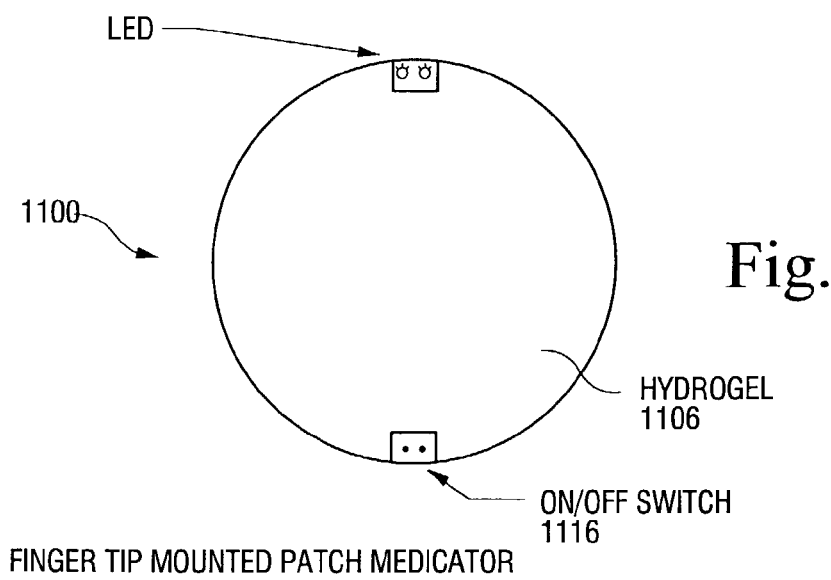

In addition, the PCB arrangement may be applied to the three electrode devices shown in FIGS. 3A and 3B as illustrated in FIGS. 11A–11C. The plastic retaining ring 608 in FIG. 6B is replaced by a hydrogel retaining ring 1108 in FIG. 11B. Also added in FIG. 11B is an auxiliary electrode 1118, in the shape of a circumferential ring located directly underneath the hydrogel retaining ring 1108 but electrically separated from the treatment electrode 1110. The current source 308 and rectifying elements 320 and 322 in FIGS. 3A and 3B are not explicitly shown in FIGS. 11A–11C but rather, are included in components 1112. Because the PCB arrangement is most amenable to implementation of segmented treatment electrode for alleviation of current concentration, the design of FIG. 3B is explicitly illustrated in FIG. 11A as containing a multitude of treatment electrodes. Current limiters 319 in FIG. 3B for current partitioning are implicit in components 1112 of FIG. 11B. FIGS. 11A–11C thus demonstrate the PCB arrangement can be readily applied to the three electrode devices shown in both FIGS. 3A and 3B. The three electrode PCB arrangement may be used in the patch medicator, the finger-splint device of FIGS. 9A and 9B, and the finger-mounted device of FIG. 10, as well as the other devices described in application Ser. Nos. 09/523,217; 09/584,138; 10/117,346; and 10/245,337.

While the invention has been described in connection with what is presently considered to be the most practical and preferred embodiment, it is to be understood that the The invention is not to be limited to the disclosed embodiment, but on the contrary, is intended to cover various modifications and equivalent arrangements included within the spirit and scope of the appended claims.

The invention claimed is:

1. A method of treatment by electrokinetic self-administration of a medicament into a treatment site for an individual, comprising:
   providing a device shaped in part to conform to at least a portion of an individual's finger and having a self-contained alternating current power source, a treatment electrode, an auxiliary electrode and a counter electrode;
   releasably retaining the device on the individual's finger with the counter electrode in electrical contact with the individual's finger;
   while the device remains on the individual's finger, placing the treatment electrode in electrical contact with the individual's treatment site with the medicament interposed between the treatment electrode and the treatment site; and
   supplying current to said electrodes when said electrodes are in electrical contact with the body so that a unidirectional current flow for delivering the medicament into the body is maintained through the treatment electrode at the treatment site and a bidirectional current flow is maintained through the body.

2. A method according to claim 1 including providing the treatment electrode, the counter electrode, and the auxiliary electrode stacked relative to one another between the individual's finger and the treatment site during treatment.

3. A method of treatment by electrokinetic self-administration of a medicament into a treatment site for an individual, comprising:
   providing an applicator having a self-contained alternating current power source, a treatment electrode and an auxiliary electrode on one side of said applicator and a counter electrode on an opposite side thereof;
   interposing the applicator between an individual's finger with the counter electrode in electrical contact with the individual's finger and the treatment site, the treatment electrode in electrical contact with the treatment site and with the medicament disposed between the treatment electrode and the treatment site and the auxiliary electrode in electrical contact with a portion of the individual's body adjacent the treatment site and through at least one of the medicament or an electrical conductor; and
   supplying current to said electrodes when said electrodes are in electrical contact with the body so that a unidirectional current flow for delivering the medicament into the body is maintained through the treatment electrode at the treatment site and a bidirectional current flow is maintained through the body.

4. A method according to claim 3 including providing the treatment electrode divided into sub-electrodes and providing current limiters associated with each sub-electrode.

5. A method according to claim 4 including providing the treatment electrode, the counter electrode, and the auxiliary electrode stacked relative to one another between the individual's finger and the treatment site during treatment.

6. A method according to claim 3 including, prior to step (b), adhering the applicator to the individual's finger.

7. A method according to claim 3 including activating the device to supply the electrical current, deactivating the device to cut off the electrical current, and reusing the device by repeating steps (b) and (c).

8. A method according to claim 7 including counting the number of treatment cycles for which the applicator has been used and permanently deactivating the applicator after the count reaches a predetermined number of treatments.

9. A method according to claim 7 including disabling the applicator for a predetermined time period to prevent reuse of the applicator for said predetermined time period after a preceding use.

10. An electrokinetic delivery system for administering a medicament to a treatment site on an individual, comprising:
    an applicator having a self-contained alternating current source and a plurality of electrodes;
    at least one of said electrodes being carried by said applicator adjacent one side thereof;
    at least one auxiliary electrode carried by said applicator adjacent said one side and electrically separated from said one electrode;
    a counter electrode adjacent a side of said electrode remote from said one side for electrical engagement with an individual's fingertip; and
    circuitry connected between the alternating current source and the electrodes for supplying current to said electrodes when said electrodes are in electrical contact with the individual's body and with the medicament interposed between the one electrode and the body so that a unidirectional current flow for delivering the medicament into the body is maintained through the one electrode at the treatment site and a bidirectional current flow is maintained through the body.

11. A system according to claim 10 wherein said electrodes are stacked relative to one another between the individual's fingertip and the treatment site.

12. A method according to claim 11 including providing the treatment electrode divided into sub-electrodes and providing current limiters associated with each sub-electrode.

13. A system according to claim 10 wherein said one electrode is divided into sub-electrodes and said circuitry includes current limiters respectively associated with each sub-electrode.

14. A method of treatment by electrokinetic self-administration of a substance into a treatment site of an individual, the method comprising:
    (a) providing an applicator including processing circuitry, a counter electrode and a treatment electrode, wherein the treatment electrode and counter electrode are formed on opposite sides of the applicator; a substance in contact with the treatment electrode and adapted for electrical contact with the user's body at the treatment site; and a conductive gel in contact with the counter electrode and adapted for electrical contact with a user's finger;
    (b) releasably retaining the applicator on the individual's finger, with the conductive gel in electrical contact with the individual's finger;
    (c) while the applicator remains retained on the individual's finger, placing the substance in contact with the treatment site; and
    (d) causing electrical current to flow through said treatment electrode, the substance, the treatment site, the individual's body, and said counter electrode to electrokinetically drive the substance into the treatment site.

15. An electrokinetic method for delivering a substance into a body, the method comprising:
    (a) providing a substance at a substance-delivery site on the body;

(b) placing electrodes coupled to an alternating current source in electrical contact with the body, the electrodes including a treatment electrode divided into sub-electrodes and adapted for electrical contact with the body at the substance-delivery site; and (c) supplying current to said electrodes when said electrodes are in electrical contact with the body so that a uni-directional current flow for delivering the substance into the body is maintained through said treatment electrode at the substance-delivery site and a bi-directional current flow is maintained through the body.

16. The method according to claim 15, wherein said alternating current source has a frequency of about 100 kilohertz.

17. The method according to claim 15, wherein said alternating current source has a frequency between about 1 kilohertz and 1 megahertz.

18. The method according to claim 15, wherein the uni-directional current is generated using a diode.

19. The method according to claim 15, wherein the substance is one or more substances selected from the group consisting of: abacavir, adefovir, amprenavir, azidothymidine, brivudin, cidofovir, delaviridine, didanosine, doxorubican, efavirenz, famciclovir, flucytosine, fluorouracil, ganciclovir, griseofulin, indinavir, ketoconazole, lamivudine, lobucavir, methotrexate, metronidazole, miconazole, n-docosanol, nelfinavir, nevirapine, nystatin, penciclovir, ribavirin, ritonavir, saquinavir, sorivudine, stavudine, tacrolimus, terbinafine HCL, trifluridine, valaciclovir, zalcitabine with or without a C21–C28 aliphatic alcohol.

20. A method according to claim 15 including applying steps (a)–(c) for treating clinical conditions caused by Herpes Simplex virus infection.

21. A method according to claim 15 including applying steps (a)–(c) for treating clinical conditions suspected to be caused by Herpes Simplex virus infection.

22. A method according to claim 15 including applying steps (a)–(c) for treating clinical conditions suspected to be caused by or caused by acne.

23. A method according to claim 15 including applying steps (a)–(c) for treating clinical conditions caused by human papilloma virus.

24. A method according to claim 15 including applying steps (a)–(c) for treating skin wrinkles.

25. A system for delivering a substance into a body at a treatment site, said system comprising:
    a finger applicator comprising processing circuitry including a counter electrode and a treatment electrode, wherein the treatment electrode and counter electrode are formed on opposite sides of the applicator, said processing circuitry including one of a microprocessor, a microcontroller, an ASIC or a programmable logic array;
    a substance in contact with the treatment electrode and adapted for electrical contact with the user's body at the treatment site;
    a conductive gel in contact with the counter electrode and adapted for electrical contact with a user's finger.

26. The system according to claim 25, wherein the substance is one or more substances selected from the group consisting of: abacavir, adefovir, amprenavir, azidothymidine, brivudin, cidofovir, delaviridine, didanosine, doxorubican, efavirenz, famciclovir, flucytosine, fluorouracil, ganciclovir, griseofulin, indinavir, ketoconazole, lamivudine, lobucavir, methotrexate, metronidazole, miconazole, morphine, n-docosanol, nelfinavir, nevirapine, nystatin, penciclovir, ribavirin, ritonavir, saquinavir, sorivudine, stavudine, tacrolimus, terbinafine HCL, trifluridine, valaciclovir, zalcitabine with or without a C21–C28 aliphatic alcohol.

27. The system according to claim 25, wherein the substance comprises estrogen or estrogen analogues.

28. The system according to claim 25, wherein the substance comprises a modulator of collagen deposition.

29. The system according to claim 25, wherein the substance comprises one or more substance selected from the group consisting of: lidocaine, xylocaine, prontocaine, prilocaine, fetanyl, remifentanil, sufentanil, alfentanil, novocaine, procaine, morphine HCL and EMLA.

30. The system according to claim 25, wherein the substance comprises one or more substances selected from the group consisting of: ketorolac, benzoyl peroxide, clindamycin phosphate (cleocin), erythromycin, tazarotene, adapalene, and azelaic acid.

31. The system according to claim 25, wherein the substance comprises one or more substances from the group consisting of: imiquimod, acyclovir, sodium salicylate, salicylic acid, tretinion, benzoyl peroxide, bleomycin, interferons, and Podocon-25.

32. The system according to claim 25, wherein the processing circuitry prevents operation of the system after a predetermined number of uses of the device.

33. The system according to claim 25, wherein the processing circuitry prevents further operation of the system after a predetermined time duration corresponding to an aggregate total time usage.

34. The system according to claim 25, wherein the processing circuitry inactivates the system for a predetermined time period and reactivates the applicator after the predetermined time period.

35. The system according to claim 25, wherein the system is configured as a patch.

36. The system according to claim 25, wherein the system is finger-mounted.

37. A method according to claim 15 including applying steps (a)–(c) for treating clinical conditions caused by or suspected to be caused by onychomycosis.

38. A method according to claim 14 including applying steps (a)–(d) for treating clinical conditions caused by or suspected to be caused by onychomycosis.

39. A method according to claim 14 including applying steps (a)–(d) for treating clinical conditions caused by Herpes Simplex virus infection.

40. A method according to claim 14 including applying steps (a)–(d) for treating clinical conditions suspected to be caused by Herpes Simplex virus infection.

41. A method according to claim 14 including applying steps (a)–(d) for treating clinical conditions caused by acne.

42. A method according to claim 14 including applying steps (a)–(d) for treating clinical conditions caused by human papilloma virus.

43. A method according to claim 14 including applying steps (a)–(d) for treating skin wrinkles.

44. The method according to claim 14, wherein the system is configured as a patch.

45. The method according to claim 14, wherein the system is finger-mounted.

46. A method according to claim 14 wherein said substance includes one of ketoconazole, nystatin, griseofulin, flucytosine and metronidazole.

* * * * *